US008980838B2

(12) United States Patent
Wang et al.

(10) Patent No.: US 8,980,838 B2
(45) Date of Patent: Mar. 17, 2015

(54) CYCLIZED PEPTIDOMIMETIC SMALL MOLECULE INHIBITORS OF THE WDR5 AND MLL1 INTERACTION

(71) Applicant: The Regents of the University of Michigan, Ann Arbor, MI (US)

(72) Inventors: Shaomeng Wang, Saline, MI (US); Hacer Karatas, Ann Arbor, MI (US); Yali Dou, Ann Arbor, MI (US); Elizabeth Townsend, Ann Arbor, MI (US); Denzil Bernard, Ann Arbor, MI (US); Fang Cao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/686,475

(22) Filed: Nov. 27, 2012

(65) Prior Publication Data

US 2013/0150309 A1    Jun. 13, 2013

Related U.S. Application Data

(60) Provisional application No. 61/564,156, filed on Nov. 28, 2011.

(51) Int. Cl.
| | | |
|---|---|---|
| *A61K 38/12* | (2006.01) | |
| *A61P 35/00* | (2006.01) | |
| *C07K 5/12* | (2006.01) | |
| *A61K 45/00* | (2006.01) | |
| *A61N 5/10* | (2006.01) | |
| *C07D 255/02* | (2006.01) | |
| *C07K 5/02* | (2006.01) | |
| *C07K 5/09* | (2006.01) | |
| *C07K 5/103* | (2006.01) | |
| *C07K 5/11* | (2006.01) | |
| *C07K 5/062* | (2006.01) | |
| *A61K 45/06* | (2006.01) | |

(52) U.S. Cl.
CPC ............... *C07K 5/126* (2013.01); *A61K 38/12* (2013.01); *A61K 45/00* (2013.01); *A61N 5/10* (2013.01); *C07D 255/02* (2013.01); *C07K 5/123* (2013.01); *C07K 5/0207* (2013.01); *C07K 5/021* (2013.01); *C07K 5/0215* (2013.01); *C07K 5/0815* (2013.01); *C07K 5/101* (2013.01); *C07K 5/1019* (2013.01); *C07K 5/06034* (2013.01); *A61K 45/06* (2013.01); *A61N 2005/1098* (2013.01)
USPC ........................................................ 514/19.9

(58) Field of Classification Search
CPC . C07K 16/2833; C07K 2317/73; A61K 38/00
See application file for complete search history.

(56) References Cited

U.S. PATENT DOCUMENTS

| | | | | |
|---|---|---|---|---|
| 2005/0026821 | A1* | 2/2005 | Pei ..................................... | 514/9 |
| 2005/0026824 | A1* | 2/2005 | Hayashi ........................... | 514/12 |
| 2009/0068224 | A1 | 3/2009 | Nakaar et al. | |

OTHER PUBLICATIONS

Argiropoulos, B., et al., "Hox Genes in Hematopoiesis and Leukemogenesis." *Oncogene* 2007, 26, 6766-6776.
Case, D.A., et al., Amber 9. In University of California: San Francisco, 2006.
Couture, J. F., et al., "Molecular Recognition of Histone H3 by the WD40 Protein WDR5." *Nat Struct Mol Biol* 2006, 13, 698-703.
De Vita, G., et al., "Expression of Homeobox Containing Genes in Primary and Metastatic Colorectal Cancer." *Eur J Cancer* 1993, 29A, 887-893.
Dou, Y., et al., "Regulation of MLL1 H3K4 Methyltransferase Activity by its Core Components." *Nat Struct Mol Biol* 2006, 13, 713-719.
Faber, J., et al., *HOXA9* is Required for Survival in Human MLL Rearranged Acute Leukemias. *Blood* 2009, 113, 2375-2385.
Ferrando, A. A., et al., "Gene Expression Signatures in MLL Rearranged T-lineage and B-Precursor Acute Leukemias: Dominance of HOX Dysregulation." *Blood* 2003, 102, 262-268.
Guenther, M. G., et al., "Global and Hox Specific Roles for the MLL1 Ethyltransferase." *Proc/Natl Acad. Sci. USA* 2005, 102, 8603-8608.
Han, Z., et al., "Structural Basis for the Specific Recognition of Methylated Histone H3 Lysine 4 by the WD-40 Protein WDR5." *Mol Cell* 2006, 22, 137-144.
Harper, D. P., et al., "Chromosomal Rearrangements Leading to MLL Gene Fusions: Clinical and Biological Aspects." *Cancer Res* 2008, 68, 10024-10027.
Hess, J. L., "MLL: a Histone Methyltransferase Disrupted in Leukemia." *Trends Mol Med* 2004, 10, 500-507.
Hombria, J. C., et al., "Beyond Homeosis—HOX Function in Morphogenesis and Organogenesis." *Differentiation* 2003, 71, 461-476.
Hsieh, J. J., et al., Proteolytic Cleavage of MLL Generates a Complex of N and C Terminal Fragments That Confers Protein Stability and Subnuclear Localization. *Mol Cell Biol* 2003, 23, 186-194.
Huntsman, D. G., et al., "MLL2, the Second Human Homolog of the *Drosophila* Trithorax Gene, Maps to 19q13.1 and is Amplified in Solid Tumor Cell Lines." *Oncogene* 1999, 18, 7975-7984.
Jenuwein, T., et al., "Translating the Histone Code." *Science* 2001, 293, 1074-1080.
Jude, C. D., et al., "Unique and Independent Roles for MLL in adult Hematopoietic Stem Cells and Progenitors." *Cell Stem Cell* 2007, 1, 324-337.
Kouzarides, T., "Chromatin modifications and Their Function." *Cell* 2007, 128, 693-705.
Maulbecker, C. C., et al., "The Oncogenic Potential of Deregulated Homeobox Genes." *Cell Growth Differ* 1993, 4, 431-441.
Mishra, B. P., et al., "Dynamic Association of MLL1, H3K4 Trimethylation with Chromatin and Hox Gene Expression During the Cell Cycle." *FEBS J* 2009, 276, 1629-1640.
Monier, B., et al., "Downstream of Homeotic Genes: in the Heart of Hox Function." *Fly* (Austin) 2007, 1, 59-67.
Nikolovska Coleska, Z., et al., Development and Optimization of a Binding Assay for the XIAP BIR3 Domain Using Fluorescence Polarization. *Anal Biochem* 2004, 332, 261-273.

(Continued)

*Primary Examiner* — Marcela M Cordero Garcia
*Assistant Examiner* — Kaipeen Yang
(74) *Attorney, Agent, or Firm* — Marshall, Gerstein & Borun LLP

(57) ABSTRACT

Cyclic peptidomimetics that inhibit the interaction between MLL1 and WDR5 are disclosed. Methods of inhibiting MLL1 activity and methods of treating cancers also are disclosed.

7 Claims, No Drawings

(56) References Cited

OTHER PUBLICATIONS

Patel, A., et al., A Conserved Arginine Containing Motif Crucial for the Assembly and Enzymatic Activity of the Mixed Lineage Leukemia Protein-1 Core Complex. *J Biol Chem* 2008, 283, 32162-32175.

Patel, A., et al., On the Mechanism of Multiple Lysine Methylation by the Human Mixed Lineage Leukemia Protein 1 (MLL1) Core Complex. *J Biol Chem* 2009, 284, 24242-24256.

Patel, A., et al., "Structure of WDR5 Bound to Mixed Lineage Leukemia Protein-1 Peptide." *J Biol Chem* 2008, 283, 32158-32161.

Ruault, M., et al., "MLLE, a New Human Member of the TRX/MLL Gene Family, Maps to 7q36, a Chromosome Region Frequently Deleted in Myeloid Leukaemia." *Gene* 2002, 284, 73-81.

Ruthenburg, A. J., et al., "Histone H3 Recognition and Presentation by the WDR5 Module of the MLL1 Complex." *Nat Struct Mol Biol* 2006, 13, 704-712.

Schuetz, A., et al., "Structural Basis for Molecular Recognition and Presentation of Histone H3 by WDR5." *EMBO J* 2006, 25, 4245-4252.

Shilatifard, A., "Molecular Implementation and Physiological Roles for Histone H3 Lysine 4 (H3K4) methylation." *Curr Opin Cell Biol* 2008, 20, 341-348.

Sims, R. J., et al., "Histone H3 Lys 4 Methylation: Caught in a Bind?" *Genes Dev* 2006, 20, 2779-2786.

Song, J. J., et al., "WDR5 Interacts with Mixed Lineage Leukemia (MLL) Protein Via the Histone H3 Binding Pocket." *J Biol Chem* 2008, 283, 35258-35264.

Trievel, R. C., et al., "WDR5, a Complexed Protein." *Nat Struct Mol Biol* 2009, 16, 678-680.

Waltregny, D., et al., Overexpression of the Homeobox Gene HOXC8 in Human Prostate Cancer Correlates with Loss of Tumor Differentiation. *Prostate* 2002, 50, 162-169.

Wysocka, J., et al., "A PHD Finger of NURF Couples Histone H3 Oysine 4 Trimethylation with Chromatin Remodelling." *Nature* 2006, 442, 86-90.

Wysocka, J., et al., WDR5 Associates with Histone H3 Methylated at K4 and is Essential for H3 K4 Methylation and Vertebrate Development. *Cell* 2005, 121, 859-872.

Karatas, Hager et al., "Analysis of the binding of mixed lineage leukemia 1 (MLL1) and histone 3 peptide to WD repeat domain 5 (WDR 5) for the design of inhibitors of the MLL1-WDR5 interaction," Journal of Medicinal Chemistry, 53(14):5179-5185 (2010).

\* cited by examiner

US 8,980,838 B2

CYCLIZED PEPTIDOMIMETIC SMALL MOLECULE INHIBITORS OF THE WDR5 AND MLL1 INTERACTION

CROSS-REFERENCE TO RELATED APPLICATIONS

This application claims the benefit of U.S. provisional patent Application No. 61/564,156, filed Nov. 28, 2011, incorporated herein by reference.

FIELD OF THE INVENTION

The present invention relates to cyclic peptidomimetic inhibitors of interactions between WDR5 (WD Repeat Domain 5) and its binding partners that interact with the Arg binding site of WDR5. More particularly, the present invention relates to cyclic peptidomimetic compounds that block MLL (mixed lineage leukemia) binding to WDR5. The present invention relates to modulation of activity resulting from a WDR5 interaction with its binding partners, including, but not limited to, activity of H3-K4 (Histone 3 Lysine 4) methylating complexes that results in H3-K4 methylation and expression of genes targeted by those complexes. The present invention also relates to the treatment of diseases and conditions related to interactions between WDR5 and its binding partners including, but not limited to, MLL.

BACKGROUND OF THE INVENTION

Histones are important in the organization of DNA into a chromatin structure and in the retrieval of genetic information. Specific modifications on histones regulate gene activity, leading to either expression or silence (1,2). Of the modifications in the euchromatins of eukaryotes that have been examined, Histone 3-Lysine 4 (H3-K4) trimethylation is recognized as a hallmark of transcriptionally active genes (3). It is believed that trimethylated H3-K4 is a recognition site for the recruitment of additional factors required for transcription (4,5). Abnormalities in H3-K4 methylating enzymes have been observed in various cancers (6,7), the most prominent example of which is Mixed Lineage Leukemia (MLL) (8), which is also known as MLL1, ALL-1, HRX, and HTRX1.

MLL is enzymatically active in a multiprotein complex and acts as both a global and a specific gene regulator (9,10). The most well-known targets for MLL are the homeobox (Hox) genes such as Hox-a9 and Hox-c8. These genes encode for a class of homeodomain transcriptional factors that regulate organ formation during embryo development, as well as proper hematopoiesis in adults (11-13). Increased expression levels of certain Hox genes, accompanied by MLL aberrations, such as gene fusion and amplification, are frequently observed in acute leukemias, such as acute lymphoblastic leukemia (ALL) and acute myeloid leukemia (AML) (14-16). Injection of cells overexpressing Hox-a7 and Hox-c8 into nude mice results in well vascularized tumors in 4-5 weeks (17). Abnormal Hox gene expression also is observed in solid tumors, such as prostate carcinoma and primary colorectal tumors (18,19). MLL therefore is a promising therapeutic target for several forms of leukemias and solid tumors.

Immediately after translation, MLL is proteolytically cleaved to yield 180-kDa C-terminus (MLL1$^C$) and 320-kDa N-terminus fragments (MLL1$^N$) (20). These are assembled together in a multi-subunit complex together with several other proteins, including WD Repeat Domain 5 (WDR5), Absent Small or Homeotic-Like (Ash2L), and Retinoblastoma Binding Protein 5 (RbBP5), each of which is a common component of all known human H3-K4 methylating complexes.

MLL forms a catalytically active core complex with WDR5, RbBP5, and Ash2L that can dimethylate H3-K4 in vitro (21). Although MLL alone can minimally partially monomethylate H3-K4, all the other members of the core complex are required for dimethylation, including WDR5, which forms a bridge between MLL and the remainder of the core complex. In the absence of WDR5, MLL is unable to associate with RbBP5 and Ash2L, and fails to dimethylate H3-K4 in vitro (21,22). Knock-down of WDR5 is known to result in a significant decrease in the levels of H3-K4 trimethylation and expression of Hox-a9 and Hox-c8 genes in 293 cells (23). Blocking of the WDR5-MLL interaction therefore is an effective strategy for inhibiting MLL activity.

It recently has been shown that MLL binds to WDR5 via an arginine (Arg) (residue 3765) containing sequence (24,25), which is similar to that used by the N-terminal of H3 in its interaction with WDR5(26-29). WDR5 has a canonical conformation that contains a central cavity, and both H3 and MLL peptides use an Arg residue to interact with this cavity through the arginine binding site. Although crystal structures show that H3 and MLL peptides have very similar binding modes to WDR5 in this arginine binding site, MLL peptides have a higher affinity to WDR5 than H3 peptides (30). The MLL-derived, 12-residue WIN (WDR5 Interacting Motif) peptide (residues 3762-3773) (Table 1) has been shown to dissociate MLL from the remainder of the complex in vitro (21). The WIN peptide therefore represents a starting point for the design of inhibitors to block the interaction of MLL with WDR5.

TABLE 1

Sequence of WIN peptide and N-terminus of H3 peptide. Residues 1-10 in H3 and 3762-3773 in MLL1 are shown. The numbering assigned below compares the residues in these two peptides.

| | | | | | | | | | | | |
|---|---|---|---|---|---|---|---|---|---|---|---|
| WIN | G | S | A | R | A | E | V | H | L | R | K | S |
| N-term of H3 | | | A | R | T | K | Q | T | A | R | K | S |
| Numbering used herein | −2 | −1 | 1 | 2 | 3 | 4 | 5 | 6 | 7 | 8 | 9 | 10 |

Abbreviations:
G—Gly—Glycine;
S—Ser—Serine;
A—Ala—Alanine;
R—Arg—Arginine;
T—Thr—Threonine;
E—Glu—Glutamic acid;
K—Lys—Lysine;
V—Val—Valine;
G—Gln—Glutamine;
H—His—Histidine;
L—Leu—Leucine.

SUMMARY OF THE INVENTION

The present invention is directed to compounds capable of inhibiting interactions of WDR5 with its binding partners through the Arg binding site in WDR5. More particularly, the present invention is directed to cyclic peptidomimetics that inhibit binding of MLL1 to WDR5. The present invention also is directed to the treatment of diseases and conditions that are mediated by the MLL-WDR5 interaction.

One aspect of the present invention relates to peptidomimetic compounds having a general formula (I):

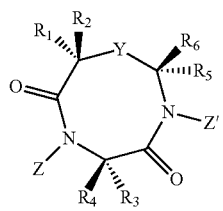

$R_1$ is selected from the group consisting of —H, substituted or unsubstituted $C_{1-9}$ alkyl, substituted or unsubstituted $C_{3-7}$ cycloalkyl, and -A-B, wherein A is selected from the group consisting of —NHC(O)—, —N($CH_3$)C(O)—, —NHS($O_2$)—, —N($CH_3$)S($O_2$)—, —CH=CH—, —C(O)—, —S($O_2$)—, —$CH_2$NH—, —NH$CH_2$—, —NH— —$CH_2$N($CH_3$)— and B is substituted or unsubstituted $C_{1-5}$ alkyl or substituted or unsubstituted $C_{3-7}$ cycloalkyl;

$R_2$, $R_5$, and $R_6$, independently, are selected from the group consisting of —H, halo, $C_{1-10}$ alkyl or $C_{3-7}$ cycloalkyl, either unsubstituted or substituted with one or more of halo, OR, SR, NRR', —$(CH_2)_n$—R'', n is 0-5, R and R', independently, are selected from the group consisting of —H, $C_{1-3}$ alkyl and $C_{3-7}$ cycloalkyl, and R'' is unsubstituted or substituted aryl or heteroaryl, or $R_1$ and $R_2$ can form a ring together with the carbon atom to which they are attached to form a $C_{3-7}$ carbocyclic ring, and, independently, $R_5$ and $R_6$ can form a ring together with the carbon atom to which they are attached to form a $C_{3-7}$ carbocyclic ring;

Z and Z', independently, are selected from the group consisting of —H, substituted or unsubstituted $C_{1-5}$ alkyl, and substituted or unsubstituted $C_{3-7}$ cycloalkyl;

$R_3$ is —$(CH_2)_m$—U, wherein m is 1-6 and U is selected from the group consisting of —$NH_2$, —$NHCH_3$, —N($CH_3$)$_2$, —$N^+(CH_3)_3$, -DQ-C(=NQ')NP'P'', where D is selected from N or CH, and Q, Q', P' and P'', independently, are H, substituted or unsubstituted $C_{1-3}$ alkyl, or substituted or unsubstituted $C_{3-7}$ cycloalkyl;

$R_4$ is selected from the group consisting of H, halo, substituted or unsubstituted $C_{1-3}$ alkyl, and substituted or unsubstituted $C_{3-7}$ cycloalkyl;

Y is substituted or unsubstituted $C_{1-20}$ alkylene or substituted or unsubstituted $C_{3-7}$ cycloalkylene, wherein one or more heteroatom S, O, P, and N, substituted or unsubstituted aryl, or substituted or unsubstituted heteroaryl optionally is inserted, -E-F-G-J-, wherein E and G, independently, are selected from the group consisting of substituted or unsubstituted $C_{1-10}$ alkyl, substituted or unsubstituted $C_{3-7}$ cycloalkyl, —C(O)NH—, —C(O)N($CH_3$)—, —S($O_2$)NH—, —S($O_2$)N($CH_3$)—, —CH=CH—, —(O)—, and —S($O_2$)—, F is selected from the group consisting of $C_{1-15}$ alkyl, substituted or unsubstituted $C_{3-7}$ cycloalkyl, and —C($R_7$)($R'_7$)—, wherein $R_7$ and $R'_7$, independently, are selected from the group consisting of H, halo, substituted or unsubstituted $C_{1-15}$ alkyl, $C_{3-7}$ cycloalkyl, phenyl, heteroaryl, and a bicyclic group, and J is substituted or unsubstituted $C_{1-15}$ alkyl or substituted or unsubstituted $C_{3-7}$ cycloalkyl, wherein one or more heteroatom, substituted or unsubstituted aryl, or substituted or unsubstituted heteroaryl optionally is inserted;

or a pharmaceutically acceptable salt or hydrate thereof.

Another aspect of the present invention is to provide cyclic peptidomimetics that inhibit WDR5 interactions with its binding partners through the arginine binding site in WDR5, i.e., where MLL and H3 proteins bind to WDR5. This embodiment includes, but is not limited to, inhibition of WDR5-MLL and WDR5-H3 interactions using the cyclic peptidomimetics of general formula (I).

Yet another aspect of the present invention is to provide a method of treating a disease or condition wherein inhibition of an interaction between WDR5 and its binding partners, including, but not limited to, MLL, provides a benefit. The method comprises administering a therapeutically effective amount of a cyclic peptidomimetic compound of the present invention to an individual in need thereof. The cyclic peptidomimetic compound can be administered as the sole therapy, or in conjunction with a therapeutically effective amount of a second agent known to be useful in the treatment of the disease or condition of interest. For example, the disease or condition can be a cancer, and the second agent is a second anticancer agent, such as radiation and/or chemotherapy.

Another aspect of this invention relates to modulation of H3-K4 methylation activity of the histone methyl transferase complexes in which WDR5 participates. Inhibition of WDR5 interactions with its binding partners, which is required for the activity of H3-K4 methylating complexes, results in disrupting their ability to methylate their targets.

Still another aspect of the present invention relates to modulation of gene expression which is controlled through H3-K4 methylation. This embodiment includes, but is not limited to, Meis-1 and Hox genes, in particular HoxA9, HoxA7, and HoxC8.

Another aspect of the present invention is to provide a method of treating a leukemia, such as acute lymphoblastic leukemia (ALL) and acute myeloid leukemia (AML), or a solid tumor, such as prostate carcinoma and primary colorectal tumors, by administering a therapeutically effective amount of a present cyclic peptidomimetic inhibitor of the MLL1-WDR5 interaction to an individual in need thereof.

Still another aspect of the present invention is to provide a cyclic peptidomimetic compound for use in therapy. Yet another aspect of the present invention is to provide cyclic peptidomimetic compounds for use in a cancer therapy, such as leukemia therapy or a solid tumor therapy.

In another aspect, the present invention provides a pharmaceutical composition comprising a present cyclic peptidomimetic compound and a pharmaceutically acceptable excipient.

Another aspect of the present invention is to utilize a cyclic peptidomimetic composition comprising a compound of structural formula (I) and a second therapeutically active agent in a method of treating an individual for a disease or condition wherein inhibition of WDR5-MLL interaction provides a benefit.

In a further embodiment, the invention provides for use of a composition comprising a cyclic peptidomimetic compound of structural formula (I) and an optional second therapeutic agent for the manufacture of a medicament for treating a disease or condition of interest, e.g., a cancer.

Still another aspect of the present invention is to provide a kit for human pharmaceutical use comprising (a) a container, (b1) a packaged composition comprising a present cyclic peptidomimetic compound, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

Another aspect of the invention is to provide fluorescently labeled tracers for WDR5 for the accurate and quantitative evaluation of the binding affinities of various compounds to WDR5. Compounds of the invention inhibit the MLL1-WDR5 interactions and therefore also are useful research tools for in vitro study of histones and their role in biological processes.

These and other aspects and features of the present invention will become apparent from the following drawings and detailed description of the preferred embodiments.

DETAILED DESCRIPTION OF THE PREFERRED EMBODIMENTS

The present invention is described in connection with preferred embodiments. It should be appreciated that the invention is not limited to these disclosed embodiments. It is understood that, given the description of the embodiments of the invention herein, various modifications can be made by a person skilled in the art. Such modifications are encompassed by the claims below.

As used herein, the terms "treat," "treating," "treatment," and the like refer to eliminating, reducing, or ameliorating a disease or condition and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms, and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; and/or relieve, to some extent, one or more of the symptoms associated with the cancer. To extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration" and similar phrases mean that two or more agents are administered concurrently to the subject being treated. By "concurrently," it is meant that each agent is administered simultaneously or sequentially in any order at different points in time. However, if not administered simultaneously, they are, in one aspect, administered sufficiently closely in time so as to provide the desired treatment effect of the combination of agents. Suitable dosing intervals and dosing order of the agents will be readily apparent to those skilled in the art. It also is contemplated that two or more agents are administered from separate compositions, and in one aspect, one composition is administered prior to administration of the other composition. Prior administration refers to administration of the agents within one day (24 hours). It is further contemplated that one agent is administered subsequent to administration of the other agent. Subsequent administration is meant to describe administration from 30 minutes of the second agent up to one day (24 hours) after administration of the first agent. Within 24 hours may include administration after 30 minutes, 1, 2, 3, 4, 5, 6, 7, 8, 9, 10, 11, 12, 16, 20, or 24 hours.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The term "binding partner" as used herein means compounds, oligomers, polymers, proteins, and related entities that interact with, e.g., bind, with the Arg binding site of WDR5.

The present invention is directed to peptidomimetic compounds have the structural formula (I):

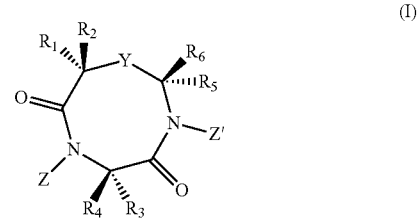

(I)

$R_1$ is selected from the group consisting of —H, substituted or unsubstituted $C_{1-9}$ alkyl, substituted or unsubstituted $C_{3-7}$ cycloalkyl, and -A-B, wherein A is selected from the group consisting of —NHC(O)—, —N(CH$_3$)C(O)—, —NHS(O$_2$)—, —N(CH$_3$)S(O$_2$)—, —CH=CH—, —C(O)—, —S(O$_2$)—, —CH$_2$NH—, —NHCH$_2$—, —NH—, —CH$_2$N(CH$_3$)— and B is substituted or unsubstituted C$_{1-5}$ alkyl or substituted or unsubstituted C$_{3-7}$ cycloalkyl;

R$_2$, R$_5$, and R$_6$, independently, are selected from the group consisting of —H, halo, C$_{1-10}$ alkyl or C$_{3-7}$ cycloalkyl, either unsubstituted or substituted with one or more of halo, OR, SR, NRR', —(CH$_2$)$_n$—R", n is 0-5, R and R', independently, are selected from the group consisting of —H, C$_{1-3}$ alkyl and C$_{3-7}$ cycloalkyl, and R" is unsubstituted or substituted aryl or heteroaryl, or R$_1$ and R$_2$ can form a ring together with the carbon atom to which they are attached to form a C$_{3-7}$ carbocyclic ring, and, independently, R$_5$ and R$_6$ can form a ring together with the carbon atom to which they are attached to form a C$_{3-7}$ carbocyclic ring;

Z and Z', independently, are selected from the group consisting of —H, substituted or unsubstituted C$_{1-5}$ alkyl, and substituted or unsubstituted C$_{3-7}$ cycloalkyl;

R$_3$ is —(CH$_2$)$_m$—U, wherein m is 1-6 and U is selected from the group consisting of —NH$_2$, —NHCH$_3$, —N(CH$_3$)$_2$, —N$^+$(CH$_3$)$_3$, -DQ-C(=NQ')NP'P''', where D is selected from N or CH, and Q, Q', P' and P''', independently, are H, substituted or unsubstituted C$_{1-3}$ alkyl, or substituted or unsubstituted C$_{3-7}$ cycloalkyl;

R$_4$ is selected from the group consisting of —H, halo, substituted or unsubstituted C$_{1-3}$ alkyl, and substituted or unsubstituted C$_{3-7}$ cycloalkyl;

Y is substituted or unsubstituted C$_{1-20}$ alkylene or substituted or unsubstituted C$_{3-7}$ cycloalkylene, wherein one or more heteroatom S, O, P, and N, substituted or unsubstituted aryl, or substituted or unsubstituted heteroaryl optionally is inserted, -E-F-G-J-, wherein E and G, independently, are selected from the group consisting of substituted or unsubstituted C$_{1-10}$ alkyl, substituted or unsubstituted C$_{3-7}$ cycloalkyl, —C(O)NH—, —C(O)N(CH$_3$)—, —S(O$_2$)NH—, —S(O$_2$)N(CH$_3$)—, —CH=CH—, —(O)—, and —S(O$_2$)—, F is selected from the group consisting of C$_{1-15}$ alkyl, substituted or unsubstituted C$_{3-7}$ cycloalkyl, and —C(R$_7$)(R'$_7$)—, wherein R$_7$ and R'$_7$, independently, are selected from the group consisting of —H, halo, substituted or unsubstituted C$_{1-15}$ alkyl, C$_{3-7}$ cycloalkyl, phenyl, heteroaryl, and a bicyclic group, and J is substituted or unsubstituted C$_{1-15}$ alkyl or substituted or unsubstituted C$_{3-7}$ cycloalkyl, wherein one or more heteroatom, substituted or unsubstituted aryl, or substituted or unsubstituted heteroaryl optionally is inserted;

or a pharmaceutically acceptable salt or hydrate thereof.

As used herein, the term "alkyl" refers to straight chained and branched saturated hydrocarbon groups, nonlimiting examples of which include methyl, ethyl, and straight chain and branched propyl, butyl, pentyl, and hexyl groups. The term C$_{n-y}$ means the alkyl group has "n" to "y" carbon atoms. An alkyl, group can be substituted with halo, trifluoromethyl, trifluoromethoxy, hydroxy, alkoxy, nitro, cyano, alkylamino, or amino groups, for example.

As used herein, the term "alkylene" refers to a hydrocarbon group containing methylene (—CH$_2$—) moieties. One or more of the methylene moieties can be substituted with a C$_{1-3}$ alkyl group, and in some embodiments, one or more of the methylene moieties can be substituted with O, S, or NR$_1$, wherein R is hydrogen or C$_{1-3}$ alkyl. "Cycloalkylene" refers to cycloalkene having two hydrogen atoms replaced by substituents, for example

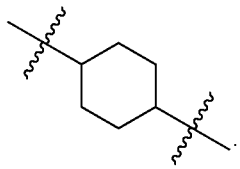 [SMILES: *C1CCC(*)CC1]

As used herein, the term "bicyclic group" refers to a substituent having two fused rings, wherein each ring, independently, contains 5 or 6 atoms selected from C, N, O, and S, and is aromatic or aliphatic.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, —(CH$_2$)$_{1-4}$halo, alkenyl, —CF$_3$, —OCF$_3$, —NO$_2$, —CN, —NC, —OH, alkoxy, —(CH$_2$)$_{1-4}$OR, —CO$_2$NR$_2$, amino, —CO$_2$H, —CO$_2$alkyl, —SR, —SO$_2$R, —SO$_3$R, aryl, and heteroaryl. Examples of heteroaryl groups include, but are not limited to, thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

As used herein, a group such as

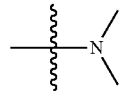

is an abbreviation for

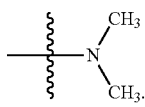

As used herein, the term "C$_{a-b}$cycloalkyl" means monocyclic aliphatic rings containing a to b carbon atoms.

As used herein, the term "halo" means fluoro, chloro, bromo, or iodo.

Cyclic peptidomimetic compounds of the invention can exist as salts. In some embodiments, pharmaceutically acceptable salts of the peptidomimetic compounds may be preferred in the methods of the invention. As used herein, the term "pharmaceutically acceptable salts" refers to salts or zwitterionic forms of the cyclic peptidomimetic compounds. Salts of the compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethanesulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In light of the foregoing, any reference to compounds of the present invention appearing herein is intended to include the cyclic peptidomimetic compounds as well as pharmaceutically acceptable salts and hydrates thereof.

MLL (mixed lineage leukemia) plays an essential role in maintaining the lineage- and differentiation stage-specific expression of HOX genes in hematopoietic cells. The function of MLL in transcription activation is mediated by its H3-K4 methyltransferase activity. MLL mutations are the major cause of a distinctive, biphenotypic leukemia of mixed identity, which account for 5-10% of AML in adults and almost 70% of ALL in infants, which have extremely poor prognostic outcomes and are associated with a diverse group of chromosomal translocations that result in distinct MLL fusion proteins. In addition to MLL translocation, MLL amplification and tandem duplications were found in acute leukemia patients. Furthermore, MLL is a well-established positive regulator of HOX genes (e.g. Hox-a9 and Meis 1), which are overexpressed in over 50% AML patients. Thus, MLL appears important for a large spectrum of leukemia cases beyond those with MLL rearrangements.

Unlike many histone methyltransferases, MLL activity is tightly regulated within a core complex containing MLL, WDR5, RbBP5, and Ash2L. While MLL alone has extremely weak activity for H3-K4 methylation, its activity can be greatly enhanced (about 100 fold) in the presence of other core components. In particular, WDR5 plays an essential role in the integrity of the MLL core complex through its direct association with MLL1 and RbBP5. Recent determination of the crystal structure of MLL peptide in complex WDR5 shows that the interaction of MLL and WDR5 is mediated by a short peptide in MLL and a well-defined binding pocket in WDR5. Disruption of the interaction between WDR5 and MLL1 leads to effective inhibition of the H3-K4 activity of MLL.

As previously discussed, mixed lineage leukemia (MLL) is a Histone 3-Lysine 4 (H3-K4) methyltransferase and is a cancer therapeutic target. The catalytic activity of MLL is regulated by the formation of a core complex consisting of MLL, WDR5, RbBP5, and Ash2L. The interaction between WDR5 and MLL plays an essential role in regulation of the H3-K4 methyltransferase activity of MLL and targeting this interaction represents an attractive therapeutic strategy.

In accordance with the present invention, the essential elements in MLL required for its high-affinity binding to WDR5 have been found. A systematic analysis of the interaction of MLL and H3 peptides with WDR5 was performed, and it was found that in the MLL derived peptides, —CO-Ala-Arg-Ala-NH— is the minimum motif for their high-affinity bonding to WDR5. The analysis further shows that intramolecular hydrogen bonds formed within this motif play a role for the high affinity bonding to WDR5.

As stated above, MLL is frequently found to be unregulated in cancers, resulting in increased expression levels of Hox target genes which link MLL with its tumorigenic properties (8,32). Consequently, inhibition of MLL activity is an attractive strategy for cancer therapy.

The MLL protein alone has minimal enzymatic activity for the mono-methylation of H3-K4 in vitro, is incapable of di- and trimethylation, and its overall catalytic activity is dramatically enhanced when it forms a core complex with WDR5, Ash2L, and RbBP5 proteins (33). Previous studies clearly established that interaction between WDR5 and MLL is required for the H3-K4 catalytic activity of the MLL core complex (21,22). Therefore, inhibition of the WDR5-MLL interaction with small-molecule inhibitors can effectively inhibit the enzymatic activity of MLL.

Having discovered the elements required for the high-affinity binding of MLL to WDR5, cyclic peptidomimetic inhibitors of the MLL-WDR5 interaction were designed, synthesized, and tested. In particular, based on the above-described studies, a series of cyclic compounds was designed and synthesized. The binding affinity of these cyclic peptidomimetics to WDR5 also was determined. The compounds and binding affinities are summarized below. Some of these compounds bind to WDR5 with high affinities and may be useful as therapeutic agents for the treatment of leukemia and other diseases in which MLL1 mis-regulation plays a role.

TABLE 1

Chemical structures of synthesized cyclic compounds and binding affinities to WDR5 as determined by fluorescence-polarization based competitive binding assay

| Code Name | Member Ring | n | R₁ | X | IC₅₀ (μM) |
|---|---|---|---|---|---|
| 4a | 12 | 4 | —H | C=O | >100 |
| 4b | 13 | 5 | —H | C=O | >100 |
| 4c | 14 | 6 | —H | C=O | >100 |
| 4d | 15 | 7 | —H | C=O | >1 |
| 4e | 16 | 8 | —H | C=O | >1 |
| 14 | 15 | 7 | C(=O)CH₃ | CH₂ | >100 |
| 15 | 15 | 7 | —H | CH₂ | >100 |

TABLE 2

Chemical structures of synthesized cyclic compounds and binding affinities to WDR5 as determined by fluorescence-polarization based competitive binding assay.

| Code Name | Member Ring | n | X | IC₅₀ (nM) |
|---|---|---|---|---|
| 19a | 14 | 2 | NH | <1000 |
| 19b | 15 | 3 | NH | <10 |
| 19c | 17 | 5 | NH | <10 |
| 29a | 16 | 1 | phenylglycine linker | <10 |
| 29b | 18 | 3 | phenylglycine linker | <10 |
| 29c | 18 | 3 | phenylglycine linker | <10 |
| 29d | 16 | 1 | N-methyl phenylglycine linker | <10 |

TABLE 2-continued

Chemical structures of synthesized cyclic compounds and binding affinities to WDR5 as determined by fluorescence-polarization based competitive binding assay.

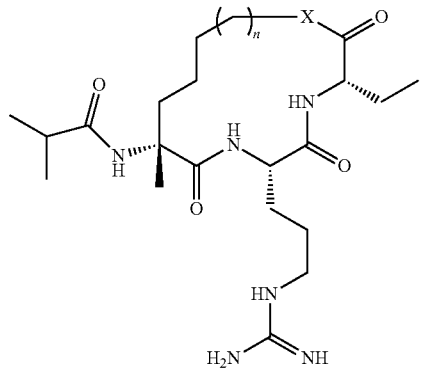

| Code Name | Member Ring | n | X | IC$_{50}$ (nM) |
|---|---|---|---|---|
| 29e | 16 | 1 | ![F-phenyl] | <10 |
| 29f | 16 | 1 | ![Cl-phenyl] | <10 |

TABLE 3

Chemical structures of synthesized cyclic compounds and binding affinities to WDR5 as determined by fluorescence-polarization based competitive binding assay.

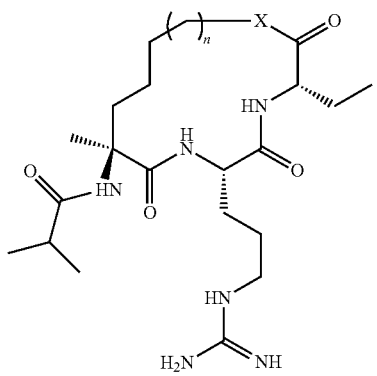

| Code Name | Member Ring | n | X | IC$_{50}$ (nM) |
|---|---|---|---|---|
| 34a | 14 | 2 | NH | <1000 |
| 34b | 15 | 3 | NH | <1000 |
| 34c | 16 | 4 | NH | <1000 |
| 34d | 17 | 5 | NH | <1000 |
| 36 | 18 | 3 | 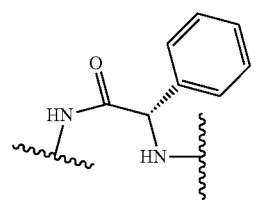 [SMILES: *NC(=O)[C@@H](N*)c1ccccc1] | <1000 |

FIG. 1. Chemical structures of cyclic peptidomimetics with different substitution on the guanidino group.

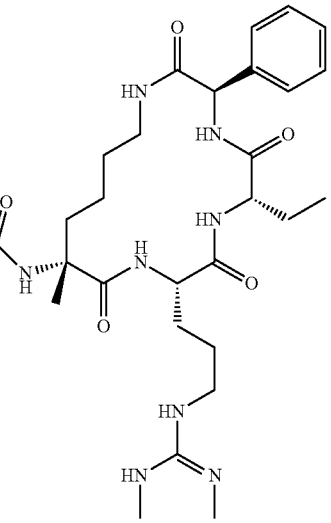

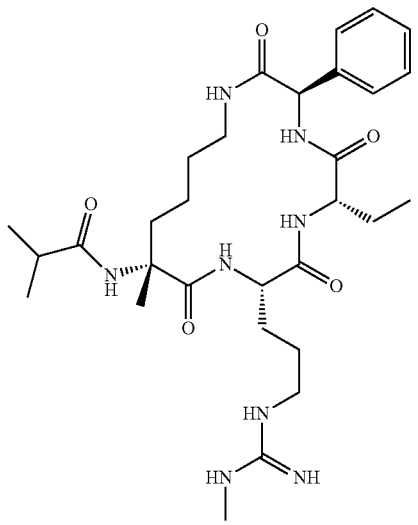
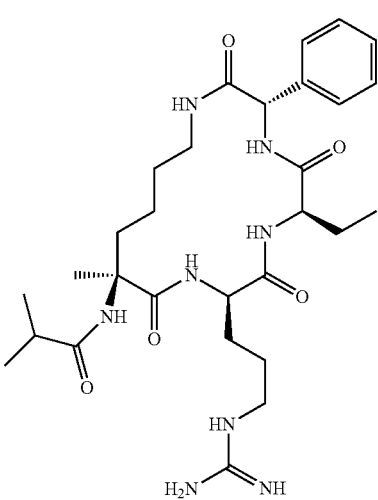
FIG. 2. Chemical structures of synthesized control compounds and binding affinities to WDR5.
FIG. 3. Chemical structures of cyclic peptidomimetics.
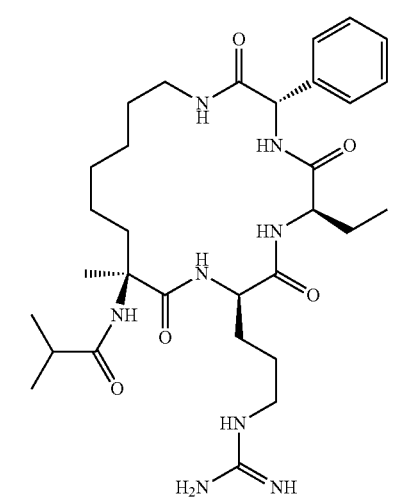
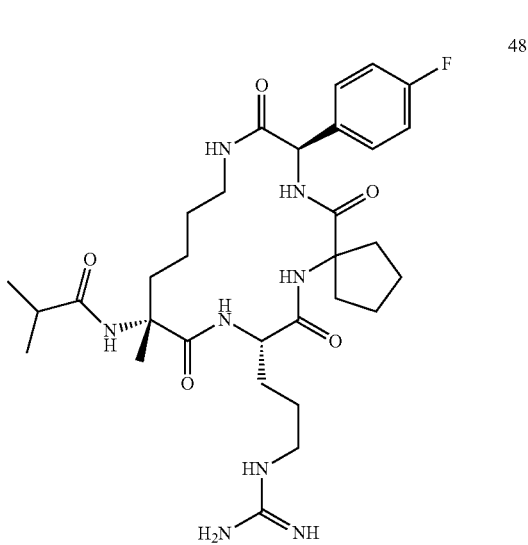
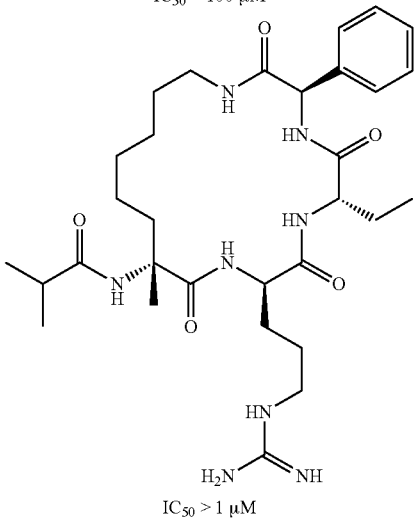
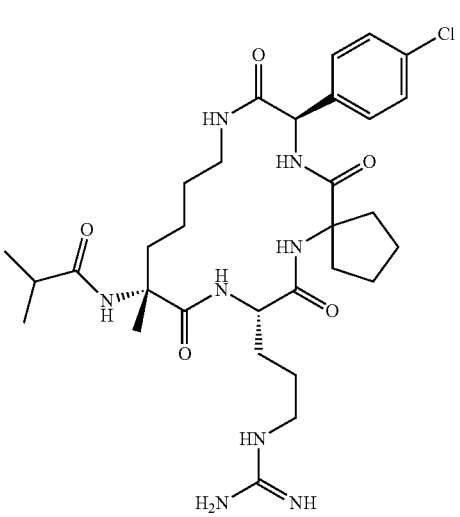

-continued
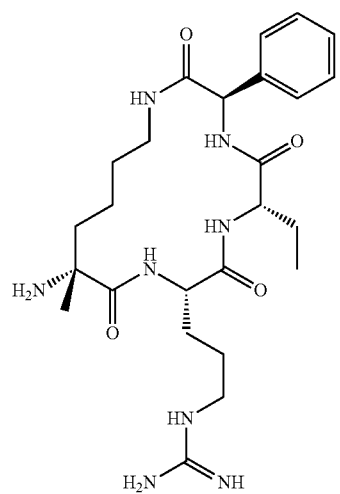
50
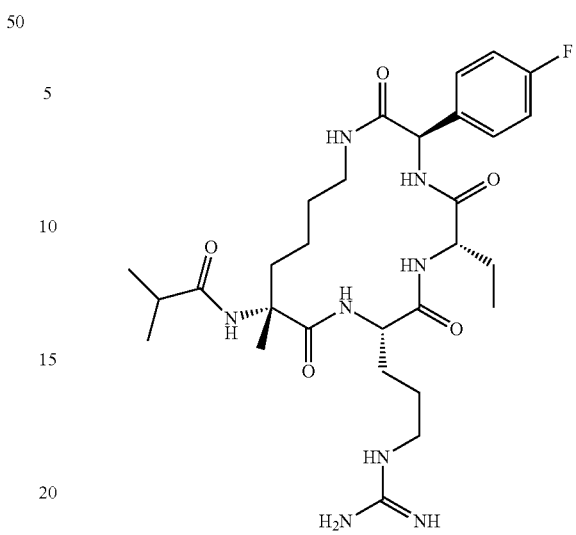
51
TABLE 4
Chemical structures and analysis of the compounds by mass spectrometry.
| Compound | Structure | Calculated (M + H)+ | Observed (M + H)+ |
|---|---|---|---|
| 4a | 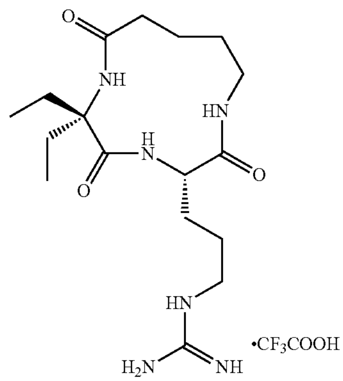 | 369.26 | 369.58 |
| 4b | 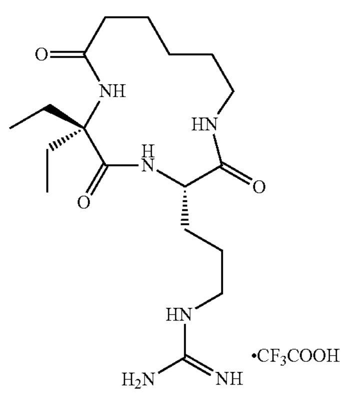 | 383.28 | 383.83 |

TABLE 4-continued

Chemical structures and analysis of the compounds by mass spectrometry.

| Compound | Structure | Calculated (M + H)+ | Observed (M + H)+ |
|---|---|---|---|
| 4c | 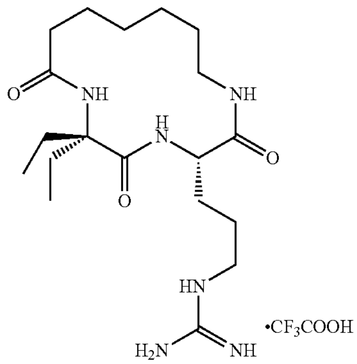 | 397.29 | 397.67 |
| 4d | 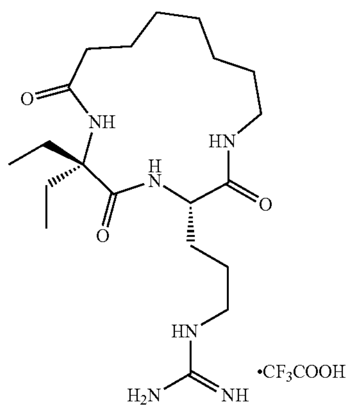 | 411.31 | 411.75 |
| 4e | 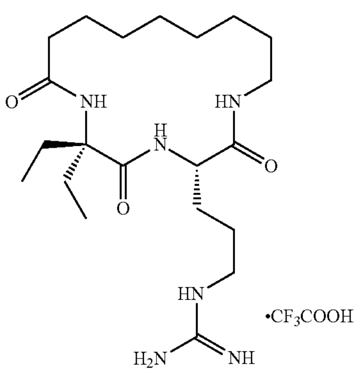 | 425.32 | 425.44 |
| 14 | 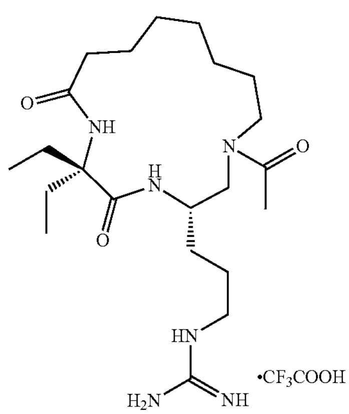 | 439.34 | 439.36 |

TABLE 4-continued

Chemical structures and analysis of the compounds by mass spectrometry.

| Compound | Structure | Calculated (M + H)+ | Observed (M + H)+ |
|---|---|---|---|
| 15 | 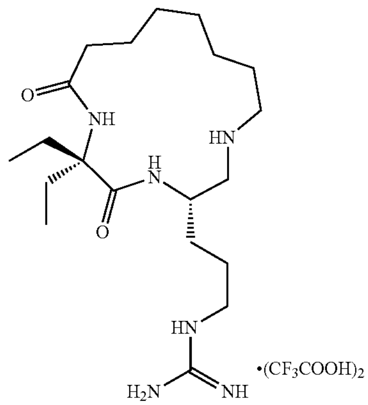 | 397.33 | 397.34 |
| 19a | 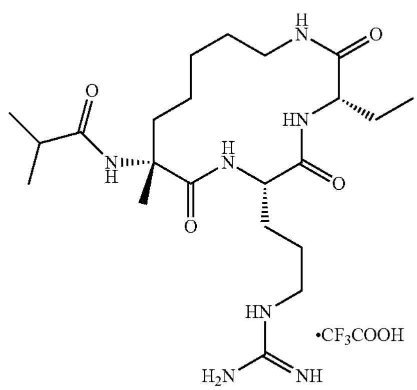 [SMILES: CC[C@@H]1NC(=O)[C@H](CCCNC(=N)N)NC(=O)[C@](C)(NC(=O)C(C)C)CCCCCNC1=O] | 468.33 | 468.36 |
| 19b | 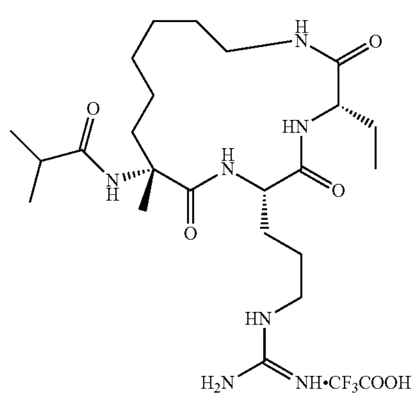 | 482.3455 | 482.3449 |

TABLE 4-continued
Chemical structures and analysis of the compounds by mass spectrometry.
| Compound | Structure | Calculated (M + H)⁺ | Observed (M + H)⁺ |
|---|---|---|---|
| 19c | 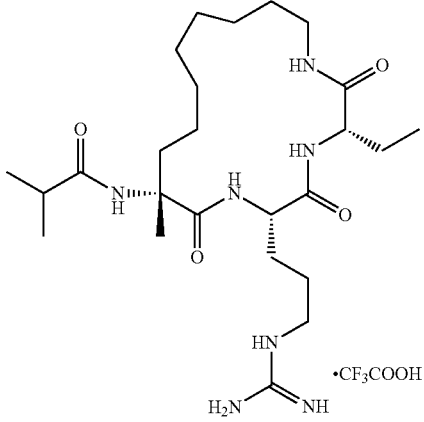 [SMILES: CC[C@@H]1NC(=O)[C@H](CCCNC(=N)N)NC(=O)[C@](C)(NC(=O)C(C)C)CCCCCCCCNC1=O ; "·CF3COOH"] | 510.38 | 510.52 |
| 29a | 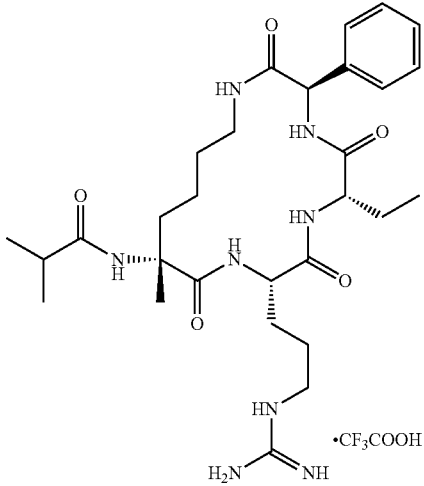 [SMILES: CC[C@@H]1NC(=O)[C@H](CCCNC(=N)N)NC(=O)[C@](C)(NC(=O)C(C)C)CCCCNC(=O)[C@@H](c2ccccc2)NC1=O ; "·CF3COOH"] | 587.37 | 587.48 |
| 29b | 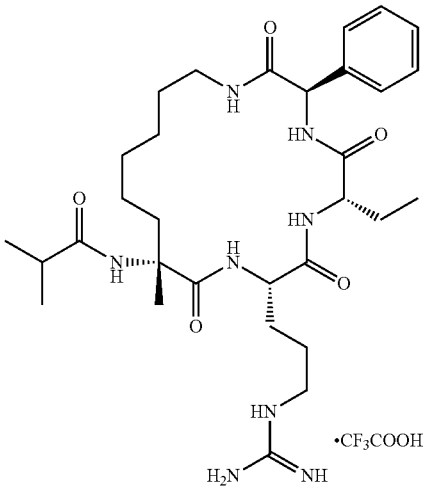 [SMILES: CC[C@@H]1NC(=O)[C@H](CCCNC(=N)N)NC(=O)[C@](C)(NC(=O)C(C)C)CCCCCCNC(=O)[C@@H](c2ccccc2)NC1=O ; "·CF3COOH"] | 615.40 | 615.46 |

TABLE 4-continued

Chemical structures and analysis of the compounds by mass spectrometry.

| Compound | Structure | Calculated (M + H)+ | Observed (M + H)+ |
|---|---|---|---|
| 29c | 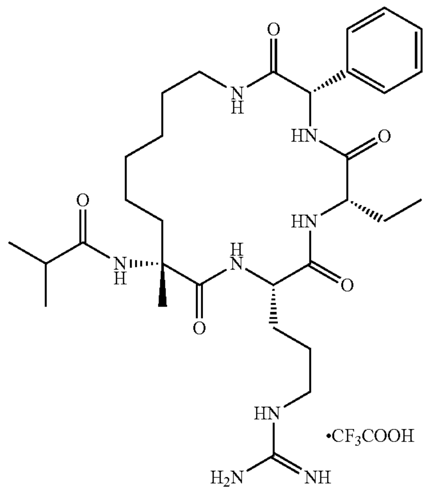 [SMILES: CC[C@@H]1NC(=O)[C@H](CCCNC(=N)N)NC(=O)[C@](C)(NC(=O)C(C)C)CCCCCCNC(=O)[C@H](c2ccccc2)NC1=O ; "·CF3COOH"] | 615.40 | 615.40 |
| 29d | 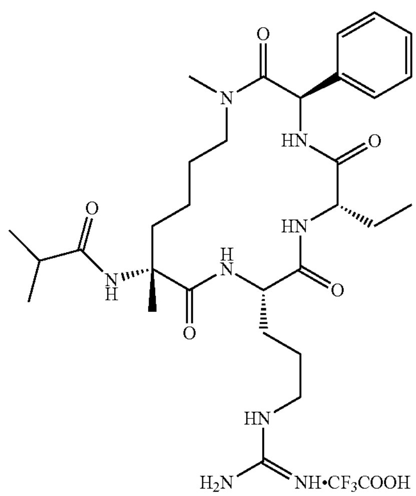 | 601.3826 | 601.3819 |
| 29e | 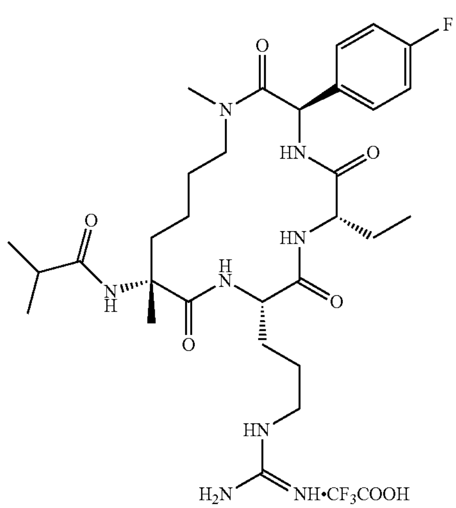 | 619.3732 | 619.3731 |

TABLE 4-continued

Chemical structures and analysis of the compounds by mass spectrometry.

| Compound | Structure | Calculated (M + H)+ | Observed (M + H)+ |
|---|---|---|---|
| 29f | 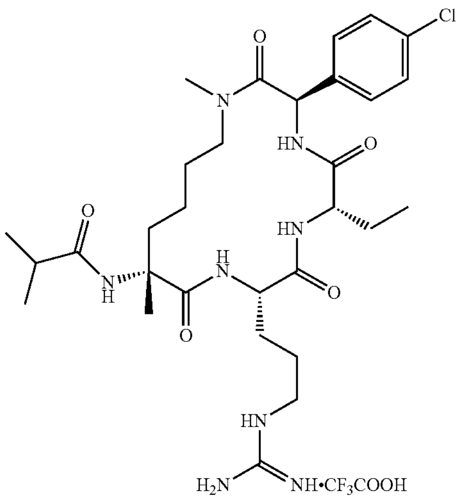 | 635.3436 | 635.3428 |
| 34a | 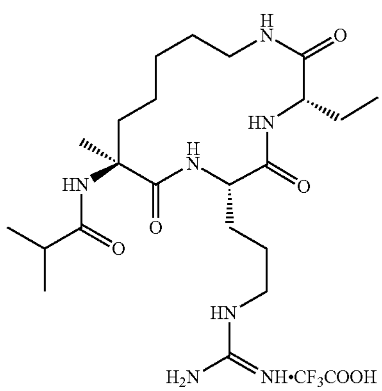 | 468.33 | 468.54 |
| 34b | 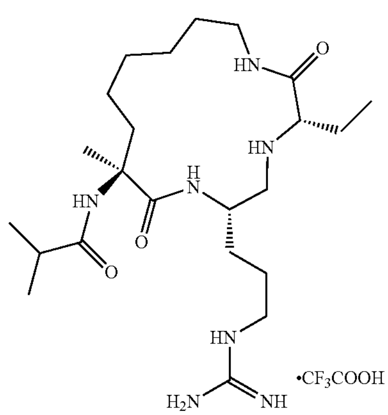 [SMILES: CC[C@@H]1NC[C@H](CCCNC(=N)N)NC(=O)[C@@](C)(NC(=O)C(C)C)CCCCCCNC1=O ; "·CF3COOH"] | 482.35 | 482.44 |

TABLE 4-continued

Chemical structures and analysis of the compounds by mass spectrometry.

| Compound | Structure | Calculated (M + H)+ | Observed (M + H)+ |
|---|---|---|---|
| 34c | 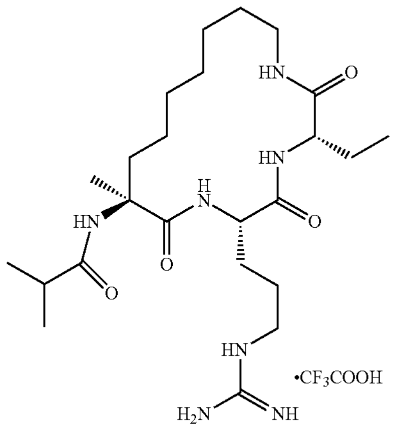 [SMILES: CC[C@@H]1NC(=O)[C@H](CCCNC(=N)N)NC(=O)[C@@](C)(NC(=O)C(C)C)CCCCCCCNC1=O ; "·CF3COOH"] | 496.36 | 496.44 |
| 34d | 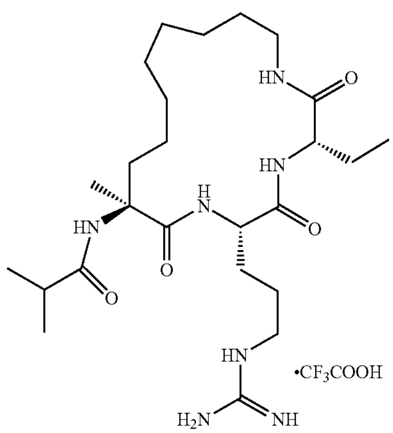 [SMILES: CC[C@@H]1NC(=O)[C@H](CCCNC(=N)N)NC(=O)[C@@](C)(NC(=O)C(C)C)CCCCCCCCNC1=O ; "·CF3COOH"] | 510.38 | 510.48 |
| 36 | 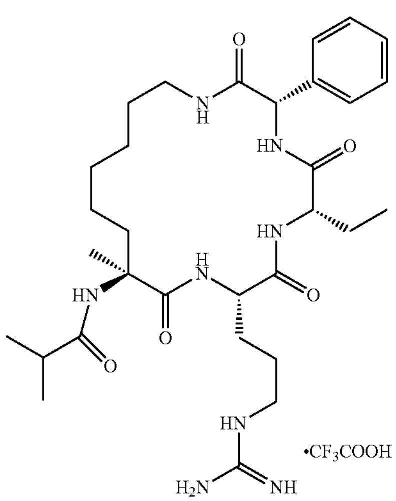 [SMILES: CC[C@@H]1NC(=O)[C@H](CCCNC(=N)N)NC(=O)[C@@](C)(NC(=O)C(C)C)CCCCCCNC(=O)[C@H](c2ccccc2)NC1=O ; "·CF3COOH"] | 615.40 | 615.50 |

TABLE 4-continued
Chemical structures and analysis of the compounds by mass spectrometry.
| Compound | Structure | Calculated (M + H)+ | Observed (M + H)+ |
|---|---|---|---|
| 40 | 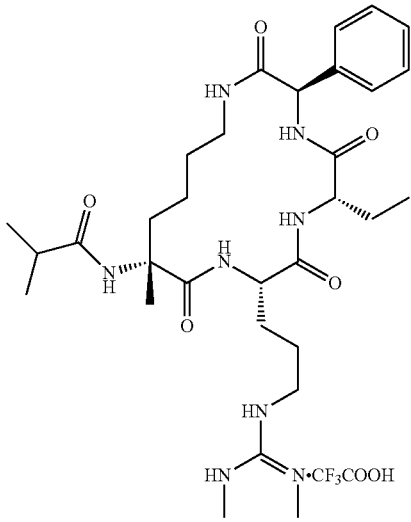 | 615.40 | 615.42 |
| 44 | 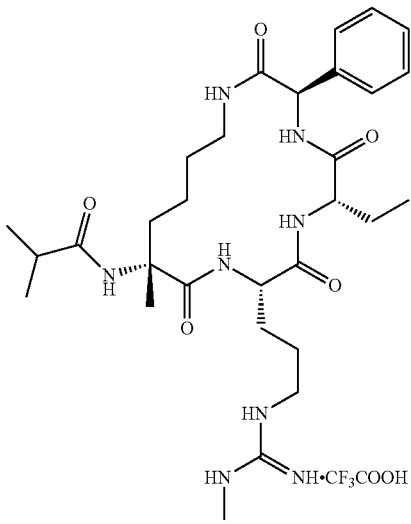 | 601.38 | 601.42 |
| 45 | 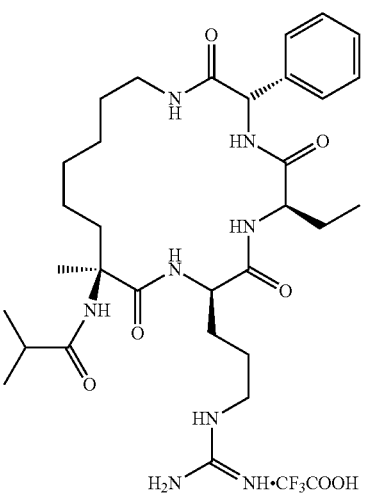 | 615.40 | 615.50 |

TABLE 4-continued

Chemical structures and analysis of the compounds by mass spectrometry.

| Compound | Structure | Calculated (M + H)+ | Observed (M + H)+ |
|---|---|---|---|
| 46 | 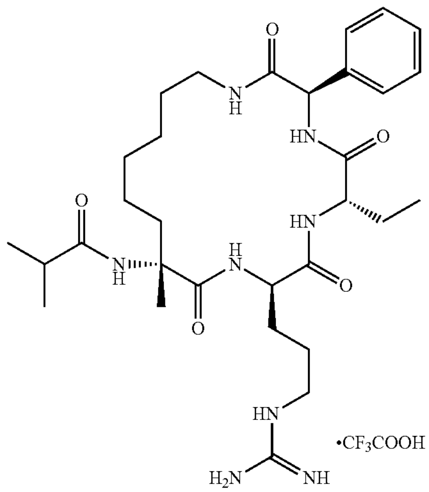 [SMILES: CC[C@@H]1NC(=O)[C@@H](CCCNC(=N)N)NC(=O)[C@](C)(NC(=O)C(C)C)CCCCCCNC(=O)[C@@H](c2ccccc2)NC1=O ; "·CF3COOH"] | 615.40 | 615.44 |
| 47 | 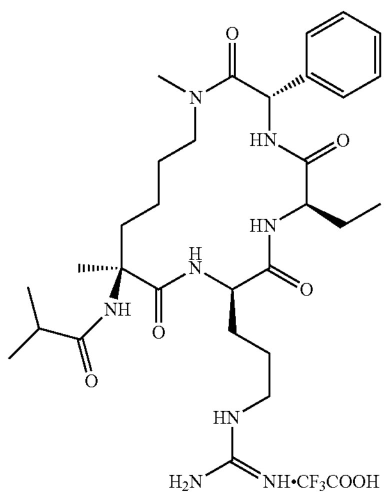 | 587.37 | 587.44 |
| 48 | 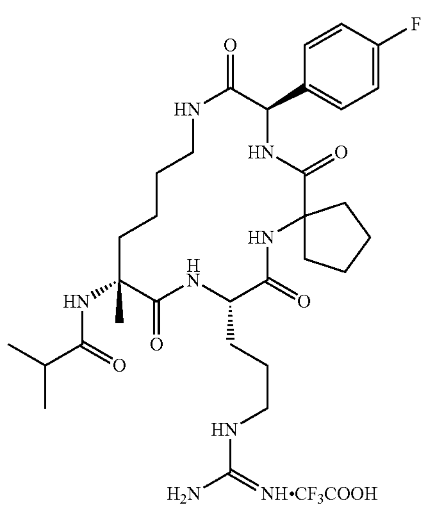 | 631.37 | 631.50 |

TABLE 4-continued

Chemical structures and analysis of the compounds by mass spectrometry.

| Compound | Structure | Calculated (M + H)⁺ | Observed (M + H)⁺ |
|---|---|---|---|
| 49 | 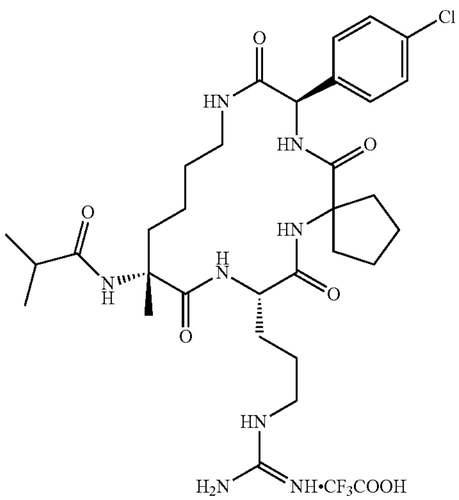 | 647.34 | 647.42 |
| 50 | 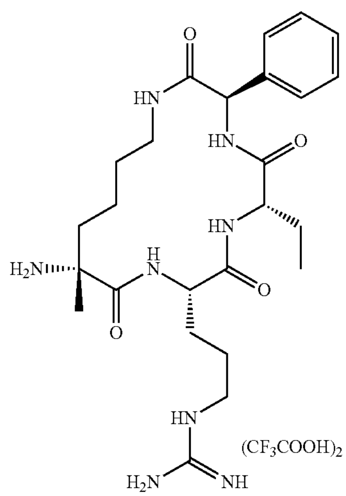 | 517.33 | 517.42 |
| 51 | 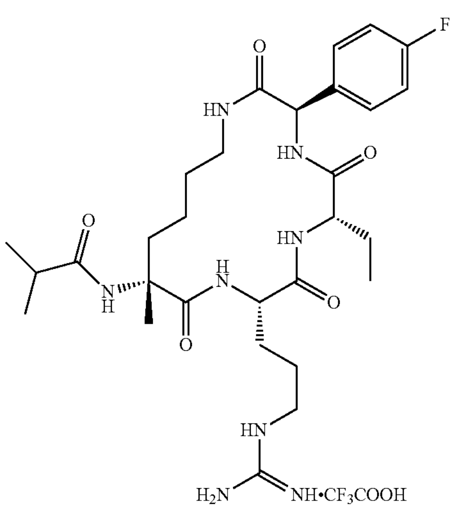 | 605.36 | 605.42 |

The present invention therefore provides inhibitors of the WDR5 interactions with its binding partners, as exemplified by the compounds disclosed herein, for the treatment of diseases and conditions wherein inhibition of the WDR5 interactions has a beneficial effect.

In one embodiment, the present invention relates to methods of treating an individual suffering from a disease or condition wherein inhibition of WDR5 interactions with its binding partners provides a benefit comprising administering a therapeutically effective amount of a present cyclic peptidomimetic compound to an individual in need thereof.

The methods described herein relate to the use of a present cyclic peptidomimetic compound useful in the treatment of diseases and conditions wherein inhibition of interactions of WDR5 with its binding partner, including but not limited to the MLL1-WDR5 interaction, provides a benefit, either alone or in conjunction with an optional second therapeutic agent useful in a treatment of the disease or condition of interest. The method of the present invention can be accomplished by administering a present cyclic peptidomimetic compound as the neat compound or as a pharmaceutical composition. Administration of a pharmaceutical composition, or neat cyclic peptidomimetic compound, can be performed during or after the onset of the disease or condition of interest. Typically, the pharmaceutical compositions are sterile, and contain no toxic, carcinogenic, or mutagenic compounds that would cause an adverse reaction when administered.

In many embodiments, a present cyclic peptidomimetic compound is administered in conjunction with a second therapeutic agent useful in the treatment of a disease or condition wherein inhibition of the WDR5 interaction with its binding partners, including but not limited to MLL, provides a benefit. The second therapeutic agent is different from a present cyclic peptidomimetic compound. A present cyclic peptidomimetic compound and the second therapeutic agent can be administered simultaneously or sequentially. In addition, a present cyclic peptidomimetic compound and the second therapeutic agent can be administered from a single composition or two separate compositions. A present cyclic peptidomimetic compound and the optional second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention also is directed to pharmaceutical compositions comprising a present cyclic peptidomimetic compound and a second therapeutic agent useful in the treatment of diseases and conditions wherein inhibition of the WDR5 interactions with its binding partners provides a benefit. Further provided are kits comprising a present cyclic peptidomimetic compound and, optionally, a second therapeutic agent useful in the treatment of diseases and conditions wherein inhibition of the WDR5 interactions with its binding partners provides a benefit, packaged separately or together, and an insert having instructions for using these active agents.

A present cyclic peptidomimetic compound and the second therapeutic agent can be administered together as a single-unit dose or separately as multi-unit doses, wherein the present cyclic peptidomimetic compound is administered before the second therapeutic agent or vice versa. One or more dose of the present cyclic peptidomimetic compound and/or one or more dose of the second therapeutic agent can be administered. The present cyclic peptidomimetic compounds therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, a present cyclic peptidomimetic compound is a potent inhibitor of the WDR5 interactions and can be used in treating diseases and conditions wherein inhibition of the WDR5 interactions with its binding partners provides a benefit.

In one embodiment, the present invention provides a method of treating a cancer comprising: (a) administering to an individual in need thereof an amount of a present cyclic peptidomimetic compound; and (b) administering to the individual an amount of radiotherapy, chemotherapy, or both. The amounts administered are each effective to treat cancer. In another embodiment, the amounts are together effective to treat the cancer.

In another embodiment, the invention provides a method for treating a cancer, said method comprising administering to a subject in need thereof a pharmaceutical composition comprising an amount of a present cyclic peptidomimetic compound effective to treat the cancer.

These therapies can be used in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

The diseases and conditions that can be treated in accordance to the invention include, for example, cancers. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderoma pigmentosum, keratoctanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the cyclic peptidomimetic compounds of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Accordingly, administration of a present cyclic peptidomimetic compound is expected to enhance treatment regimens.

Other cancers that can be treated with the compounds and methods of the invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiornyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

In the present method, a therapeutically effective amount of a cyclic peptidomimetic compound of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present cyclic peptidomimetic compound can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present cyclic peptidomimetic compound is administered in an effective amount to achieve its intended purpose. The exact formulation, route of administration, and dosage is determined by an individual physician in view of the diagnosed condition or disease. Dosage amount and interval can be adjusted individually to provide levels of a present cyclic peptidomimetic compound that is sufficient to maintain therapeutic effects.

Toxicity and therapeutic efficacy of the present cyclic peptidomimetic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present cyclic peptidomimetic compound required for use in therapy varies with the nature of the condition being treated, the length of time that activity is desired, and the age and the condition of the patient, and ultimately is determined by the attendant physician. Dosage amounts and intervals can be adjusted individually to provide plasma levels of a cyclic peptidomimetic compound that are sufficient to maintain the desired therapeutic effects. The desired dose conveniently can be administered in a single dose, or as multiple doses administered at appropriate intervals, for example as one, two, three, four or more sub-doses per day. Multiple doses often are desired, or required. For example, a present peptidomimetic compound can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present cyclic peptidomimetic compound, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present cyclic peptidomimetic compound used in a method of the present invention can be administered in an amount of about 0.005 to about 500 milligrams per dose, about 0.05 to about 250 milligrams per dose, or about 0.5 to about 100 milligrams per dose. For example, a present cyclic peptidomimetic compound can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

In the treatment of a cancer, a present cyclic peptidomimetic compound can be administered with a chemotherapeutic agent and/or radiation, or as an adjunct to surgery.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present cyclic peptidomimetic, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a peptidomimetic compound of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct antineoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 6

Alkylating agents
Nitrogen mustards mechlorethamine
cyclophosphamide
ifosfamide
melphalan
chlorambucil
uracil mustard
temozolomide
Nitrosoureas carmustine (BCNU)
lomustine (CCNU)
semustine (methyl-CCNU)
chlormethine
streptozocin
Ethylenimine/Methyl-melamine triethylenemelamine (TEM)
triethylene thiophosphoramide
(thiotepa)
hexamethylmelamine
(HMM, altretamine)

TABLE 6-continued

Alkyl sulfonates busulfan
pipobroman
Triazines dacarbazine (DTIC)
Antimetabolites
Folic Acid analogs methotrexate
trimetrexate
pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
floxuridine
pentostatine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide

TABLE 6-continued

Natural products

Antimitotic drugs
Taxanes paclitaxel
Vinca alkaloids
vinblastine (VLB)
vincristine
vinorelbine
vindesine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitromycin-C
dactinomycin
aphidicolin
epirubicin
idarubicin
daunorubicin
mithramycin
deoxy co-formycin
Enzymes L-asparaginase
L-arginase
Radiosensitizers metronidazole
misonidazole
desmethylmisonidazole
pimonidazole
etanidazole
nimorazole
RSU 1069
EO9
RB 6145
Nonsteroidal antiandrogens SR4233
flutamide
nicotinamide
5-bromodeozyuridine
5-iododeoxyuridine
bromodeoxycytidine
Miscellaneous agents
Platinum coordination complexes cisplatin
carboplatin
oxaliplatin
anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon ($\alpha$, $\beta$, $\gamma$)
interleukin-2

TABLE 6-continued

Photosensitizers hematoporphyrin derivatives
PHOTOFRIN ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792, trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminogluthimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

The cyclic peptidomimetic compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the peptidomimetic compounds.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. The composition typically can be in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present peptidomimetic compound. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present peptidomimetic compound.

When a therapeutically effective amount of a present cyclic peptidomimetic compound is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A present peptidomimetic compound can be infused with other fluids over a 10-30 minute span or over several hours.

The present cyclic peptidomimetic compounds can be readily combined with pharmaceutically acceptable carriers well-known in the art. Such carriers enable the active agents to be formulated as tablets, pills, dragees, capsules, liquids, gels, syrups, slurries, suspensions and the like. Pharmaceutical preparations can be obtained by adding a present peptidomimetic compound to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present cyclic peptidomimetic compound can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present cyclic peptidomimetic compound can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present cyclic peptidomimetic compound also can be formulated in rectal compositions, such as suppositories or retention enemas, e.g., containing conventional suppository bases. In addition to the formulations described previously, a compound also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present cyclic peptidomimetic compound and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

In accordance with an important feature of the present invention, cyclic peptidomimetic compounds were synthesized and evaluated as inhibitors for the WDR5 interactions with its binding partners. For example, compounds of the present invention typically have a bonding affinity ($IC_{50}$) to WDR5 of less than 100 µM, less than 50 µM, less than 10 µM, and less than 1 µM. It was found that the present cyclic peptidomimetic compounds are more potent, more cell permeable, and more metabolically stable than prior WDR5 inhibitors.

Procedures and Examples

Another aspect of the current invention is to develop tools to investigate role of WDR5 interaction with its binding partners including, but not limited to, MLL and H3 proteins, and the role of WDR5 in cell functions including, but not limited to, H3K4 methylation, expression of Hox genes and skeletal development. These tools can be cyclic peptidomimetics of general formula (I).

Chemistry

ABBREVIATIONS

OtBu—tertiary butoxide; Trt—trityl; Boc—tert-butoxycarbonyl; Mtt—3-(4,5-dimethyl-2-thiazolyl)-2,5-diphenyl-2H-tetrazoline bromide; Pbf—3-phenyl-benzofuranone; HOBt—1-hydroxybenzotriazole; HBTU—N-[(1H-benzotriazol-1-yl)(dimethylamino)-methylene]-methylmethanaminium hexafluorophosphate N-oxide; DIC—N,N'-diisopropylcarbodiimide; HOAt—7-aza-hydroxybenzotriazole; DMF—dimethylformamide; TFA—trifluoroacetic acid; DTT—dithiothreitol; TIS—triisopropylsilane; Fmoc—9-fluorenylmethoxycarbonyl; DIEA—diisopropylethylamine; DCM—dichloromethane; THF—tetrahydrofuran; HATU—2-(1H-7-azabenzotriazol-1-yl)-1,1,3,3-tetramethyl uronium hexafluorophosphate methanaminium; min—minute; h—hour; eq—equivalent; ml—milliliter; MeOH—methanol; IPTG—isopropyl-β-D-1-thiogalactopyranoside; KCl—potassium chloride; HEPES—(4-(2-hydroxyethyl)-1-piperazineethanesulfonic acid); PMSF—phenylmethylsulfonyl fluoride; DMSO—dimethyl sulfoxide.

Solid Phase Peptide Synthesis

Peptides were synthesized manually or with an ABI 433 Peptide synthesizer using Fmoc chemistry. Rink amide resin was used as the solid support. To avoid side reactions, amino acid residues were protected, for example as follows: Glu (OtBu), His (Trt), Lys (Boc or Mtt), Gln (Trt), Arg (Pbf), Ser (OtBu), Thr (OtBu). HOBt/HBTU or DIC/HOAt was used as the coupling reagent. HCOOH/DIC/HOAt in DMF was used for on-bead formylation where the reaction was carried out in a flask rotated overnight at room temperature using rotavapor without applying vacuum. All the peptides were cleaved from the resin using a TFA:DTT:TIS:$H_2O$ (17.5 ml:0.5 g:0.5 ml:1 ml) cleavage cocktail, which also led to removal of the protecting groups. The cleavage solution was evaporated and the crude product was precipitated with diethyl ether followed by HPLC purification using a C18 reversed phase column (Waters, SUNFIRE™ Prep C18, 19×150 mm, 5 µm). All the purified final peptides were analyzed by analytical RP-HPLC (Waters, SUNFIRE™ C18, 4.6×150 mm, 5 µm) for purity and the characterization of the peptides was determined by electrospray ionization mass spectroscopy (ESI-MS).

The cyclized peptidomimetics of the present invention were synthesized according to one of the following eight synthetic sequences. Additional synthetic sequences are envisioned and are readily practiced by persons skilled in the art.

Scheme I. Synthesis of cyclized peptides.
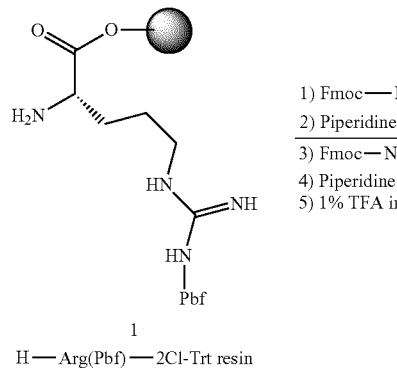
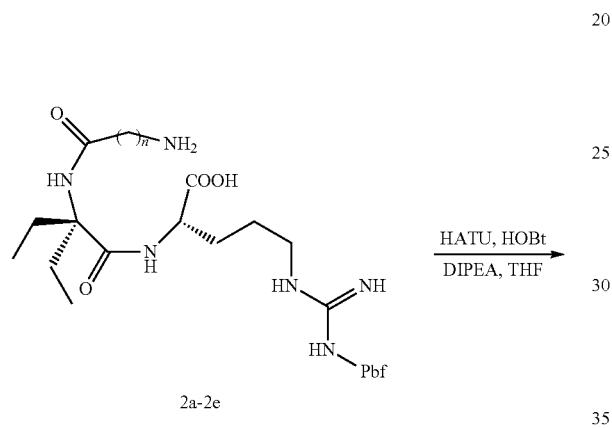
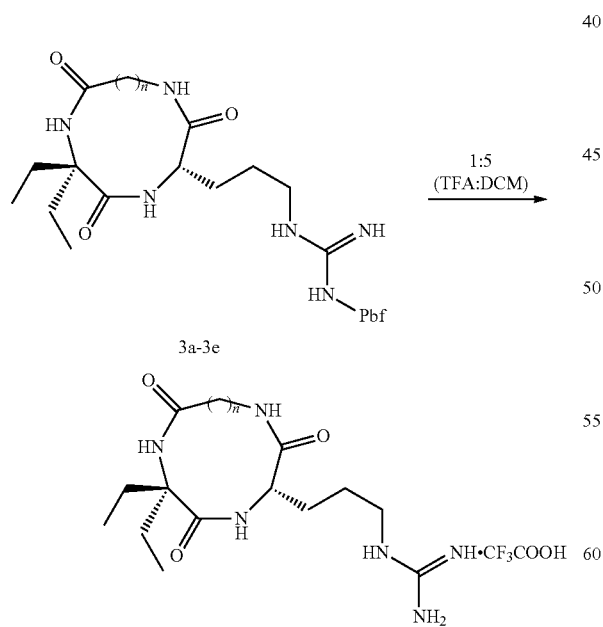

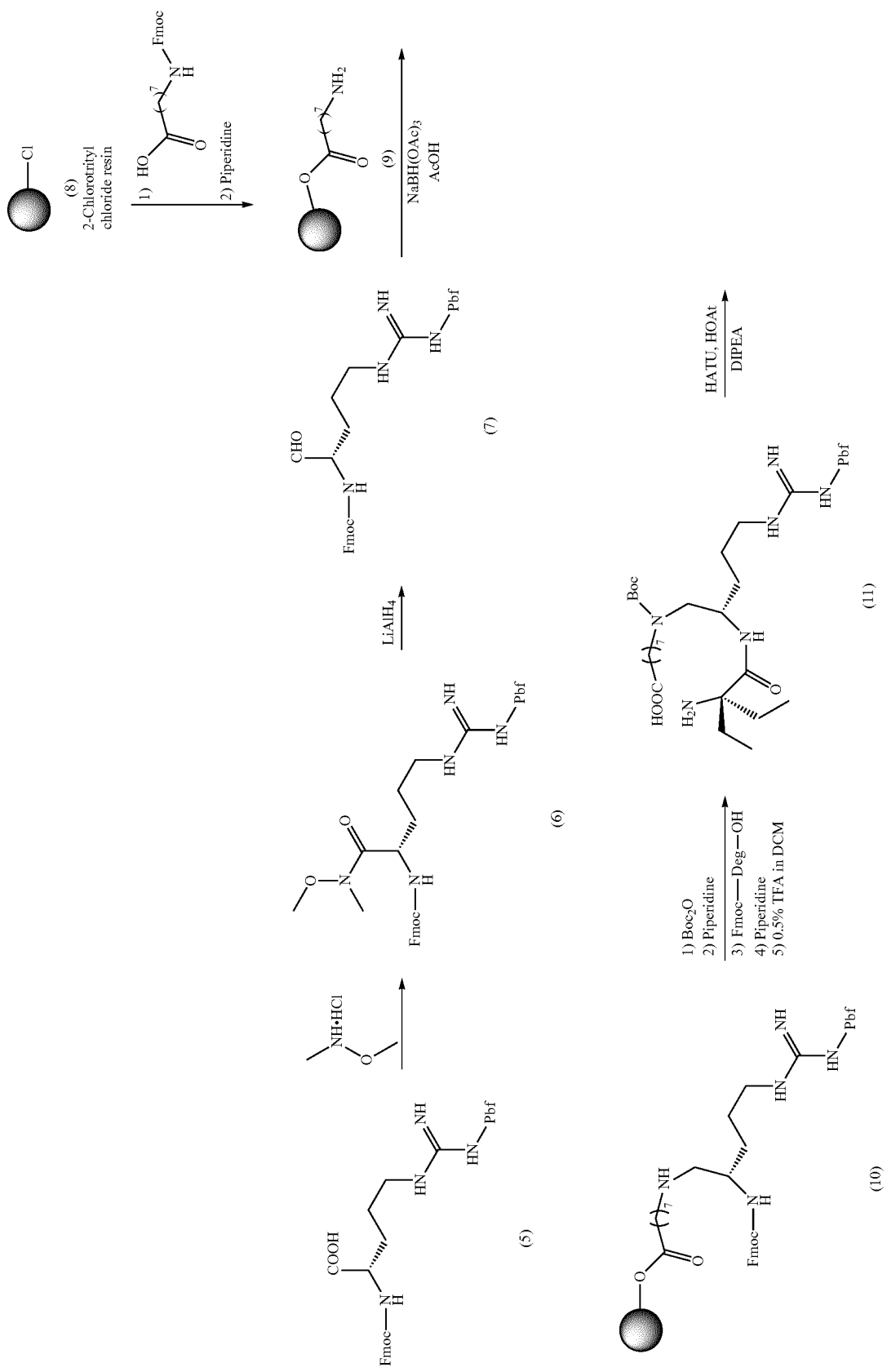

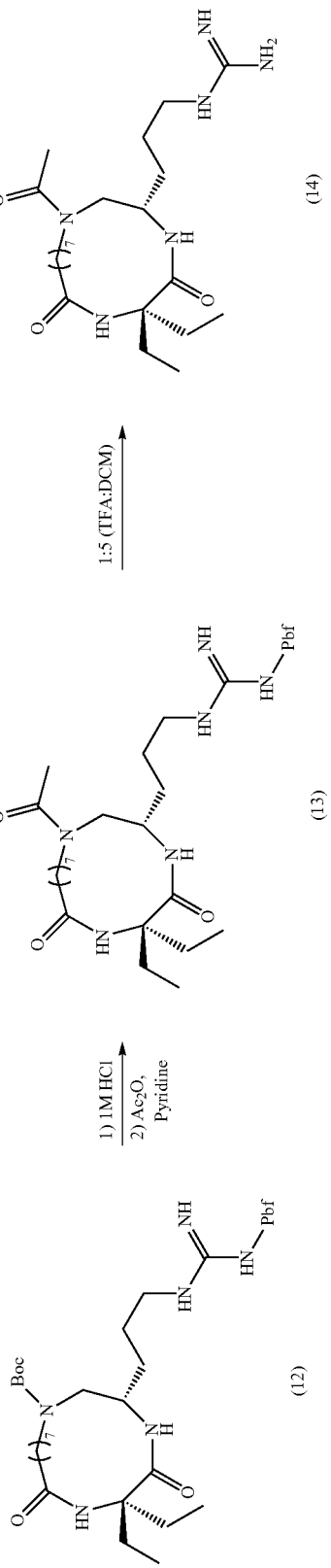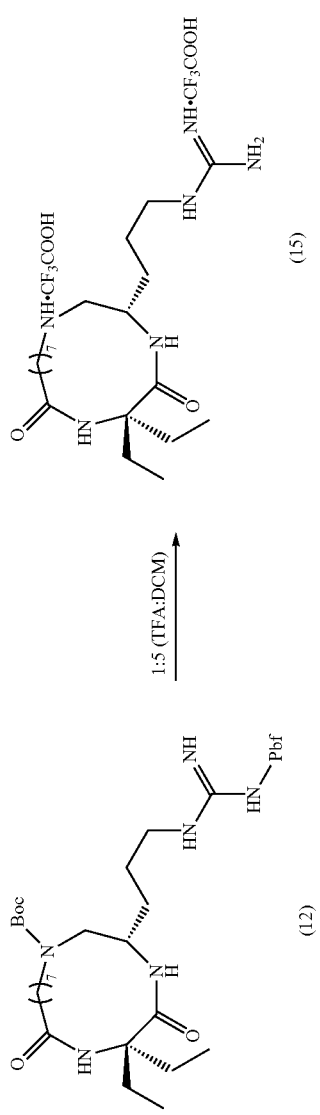

Scheme III. Synthesis of cyclized peptides.
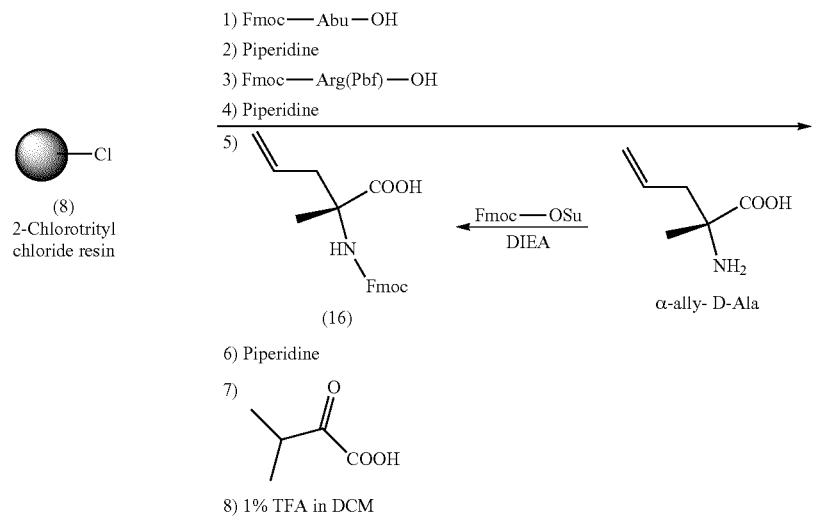
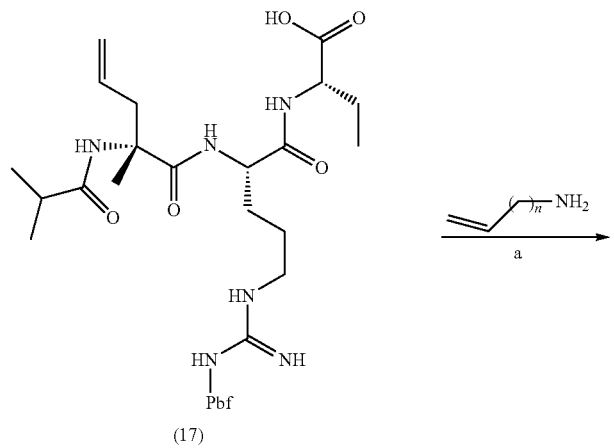
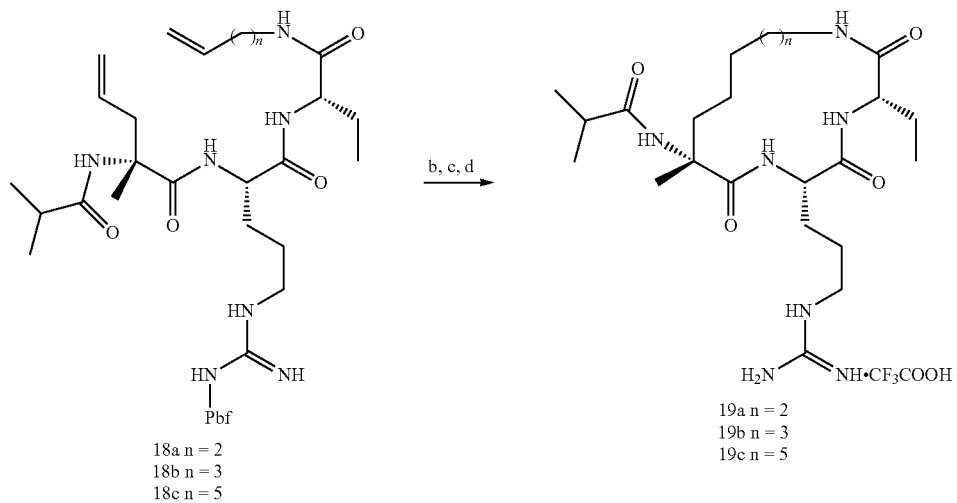
Reagents and conditions: (a) EDCl, HOAt, DIPEA, CH$_2$Cl$_2$, rt, 2-3 h; (b) Hoveyda-Grubb's 2nd generation catalyst, CH$_2$Cl$_2$, rt, overnight; (c) H$_2$/Pd•C, MeOH, rt, 2 h; (d) CH$_2$Cl$_2$:CF$_3$COOH:H$_2$O (20:10:0:5), reflux, 2 h.

Scheme IV. Synthesis of cyclized peptides.
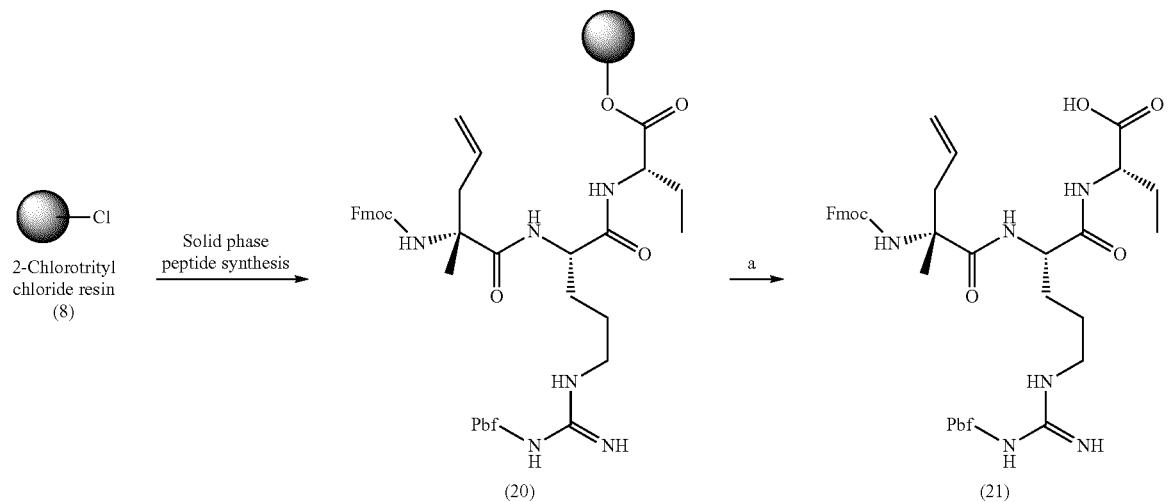
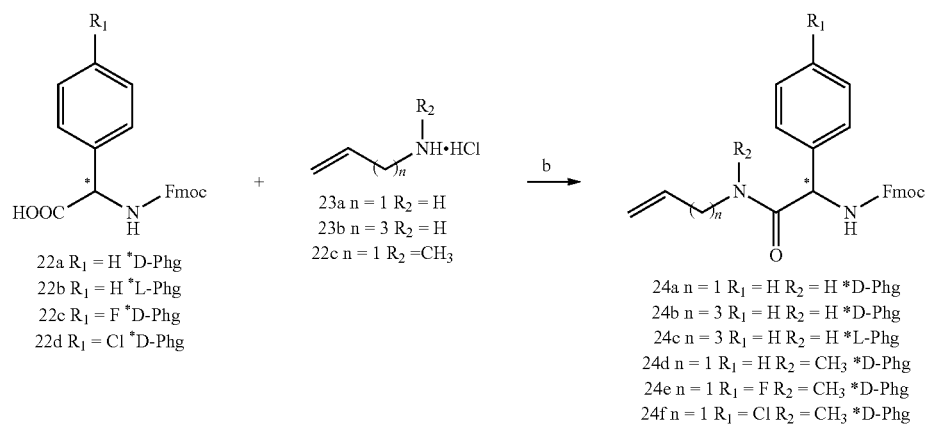
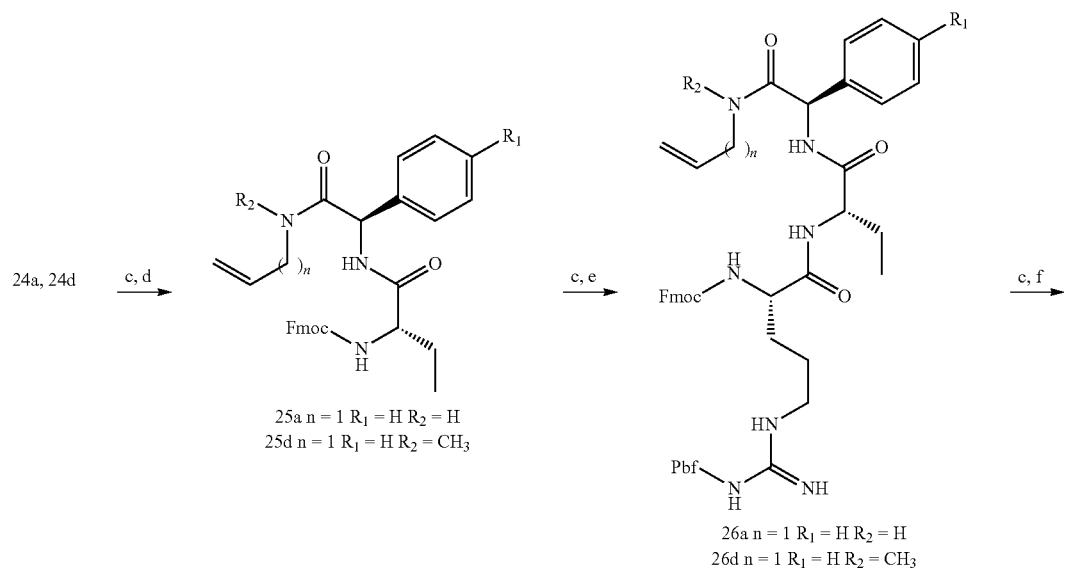

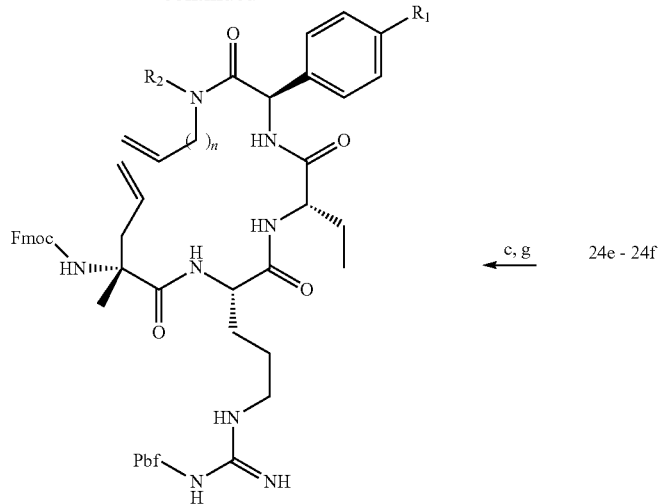
27a n = 1 R₁ = H R₂ = H
27d n = 1 R₁ = H R₂ = CH₃
27e n = 1 R₁ = F R₂ = CH₃
27f n = 1 R₁ = Cl R₂ = CH₃
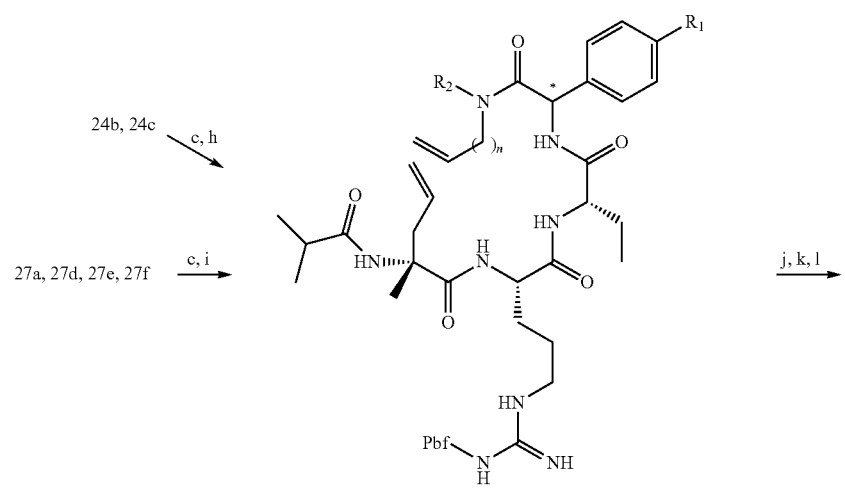
28a n = 1 R₁ = H R₂ = H *D-Phg
28b n = 3 R₁ = H R₂ = H *D-Phg
28c n = 3 R₁ = H R₂ = H *L-Phg
28d n = 1 R₁ = H R₂ = CH₃ *D-Phg
28e n = 1 R₁ = F R₂ = CH₃ *D-Phg
28f n = 1 R₁ = Cl R₂ = CH₃ *D-Phg -continued

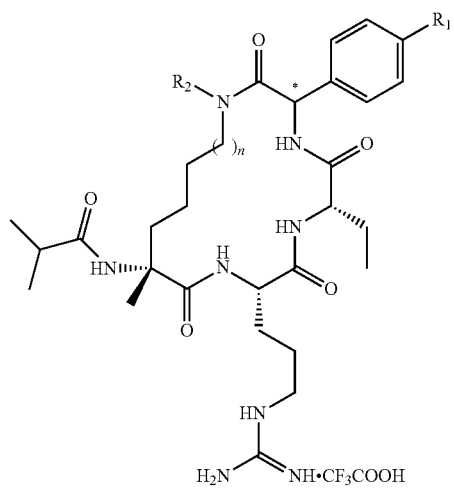

29a n = 1 R₁ = H R₂ = H *D-Phg
29b n = 3 R₁ = H R₂ = H *D-Phg
29c n = 3 R₁ = H R₂ = H *L-Phg
29d n = 1 R₁ = H R₂ = CH₃ *D-Phg
29e n = 1 R₁ = F R₂ = CH₃ *D-Phg
29f n = 1 R₁ = Cl R₂ = CH₃ *D-Phg

Reagents and conditions: (a) 1% TFA in CH₂Cl₂; (b) EDCl, HOAt, DIEA, CH₂Cl₂, rt, 2-3 h; (c) DEA, Acetonitrile, rt, 2 h; (d) Fmoc-2—Abu—OH, EDCl, HOAt, DIPEA, CH₂Cl₂, rt, 4 h; (e)Fmoc—Arg(Pbf)—OH, EDCl, HOAt, DIPEA, CH₂Cl₂, rt, 4 h; (f) (16), EDCl, HOAt, DIPEA, CH₂Cl₂, rt, 4 h; (g) (21), EDCl, HOAt. DIPEA, CH₂Cl₂, rt, 4 h; (h) (17), EDCl, HOAt, DIPEA, CH₂Cl₂, rt, 4 h; (i) isobutiryl chloride, DIPEA, CH₂Cl₂, 2 h, rt; (j) Hoveyda-Grubb's 2nd generation catalyst, CH₂Cl₂, rt, overnight; (k) H₂/Pd•C, MeOH, rt, 2 h; (l) CH₂Cl₂:CF₃COOH:H₂O (20:10:0.5), reflux, 2 h.

Scheme V. Synthesis of cyclized peptides.

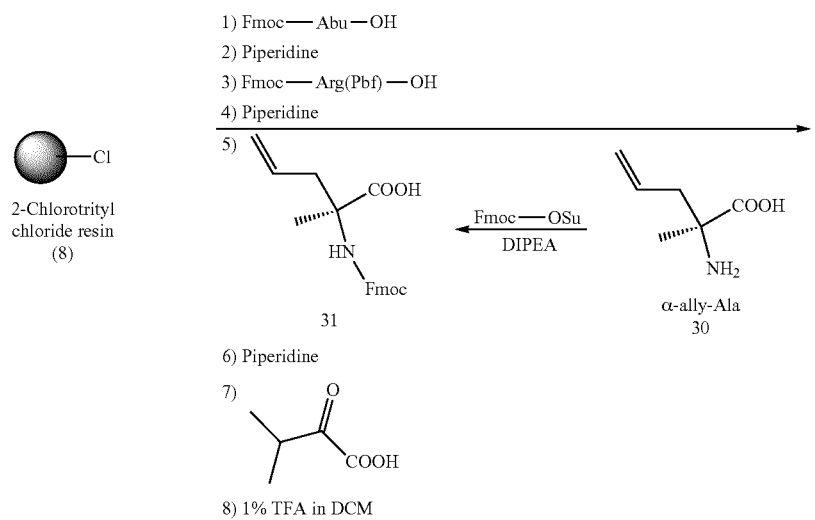

-continued
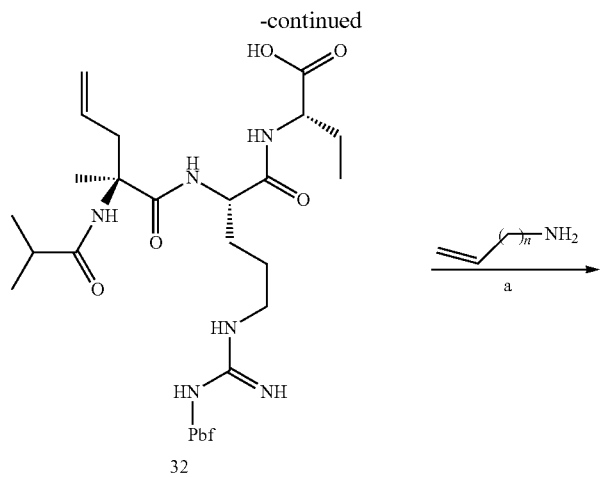
32
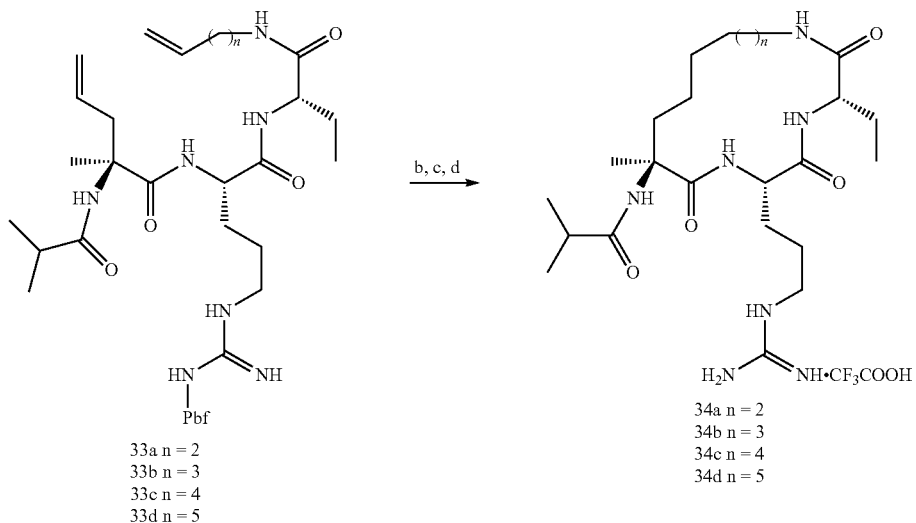
33a n = 2
33b n = 3
33c n = 4
33d n = 5
34a n = 2
34b n = 3
34c n = 4
34d n = 5
Reagents and conditions: (a) EDCl, HOAt, DIPEA, CH$_2$Cl$_2$, rt, 2-3 h; (b) Hoveyda-Grubb's 2nd generation catalyst, CH$_2$Cl$_2$, rt, overnight; (c) H$_2$/Pd•C, MeOH, rt, 2 h; (d) CH$_2$Cl$_2$:CF$_3$COOH:H$_2$O (20:10:0.5), reflux, 2 h.

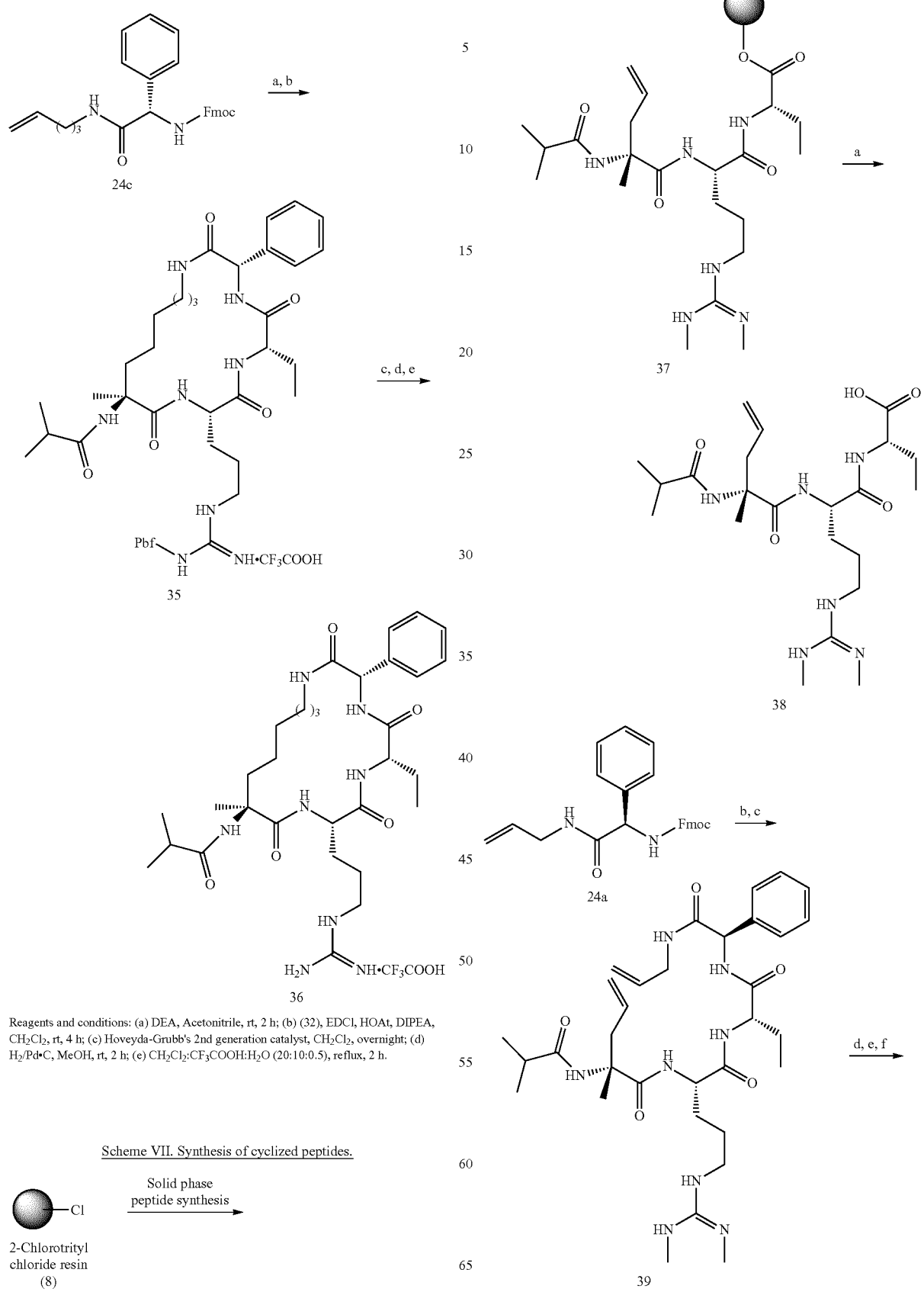

67

-continued

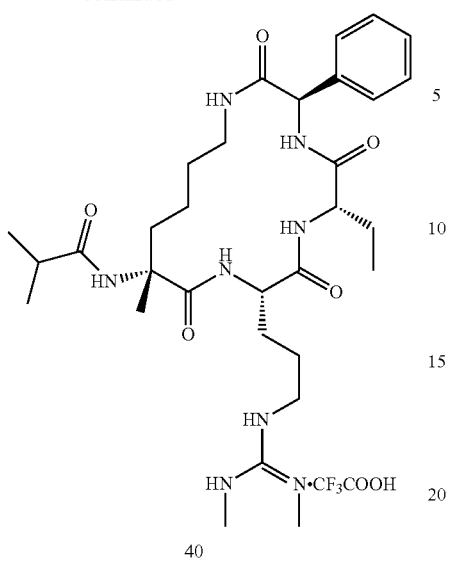

Reagents and conditions: (a) 1% TFA in CH$_2$Cl$_2$; (b) DEA, Acetonitrile, rt, 2 h; (c) (38), EDCl, HOAt, DIPEA, CH$_2$Cl$_2$, rt, 4 h; (d) Hoveyda-Grubb's 2nd generation catalyst, CH$_2$Cl$_2$, overnight; (e) H$_2$/Pd•C, MeOH, rt, 2 h; (f) CH$_2$Cl$_2$:CF$_3$COOH (1:1)

Scheme VIII. Synthesis of cyclized peptides.

68

-continued

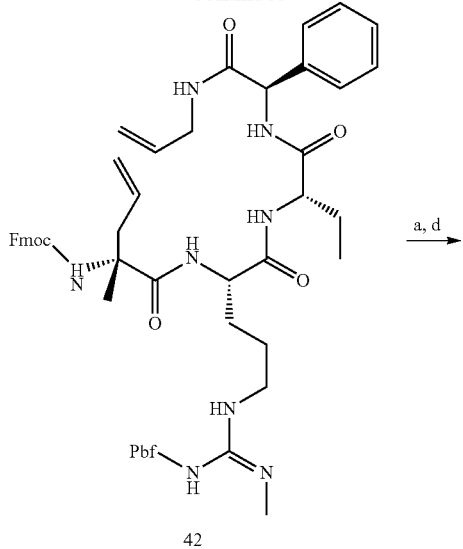

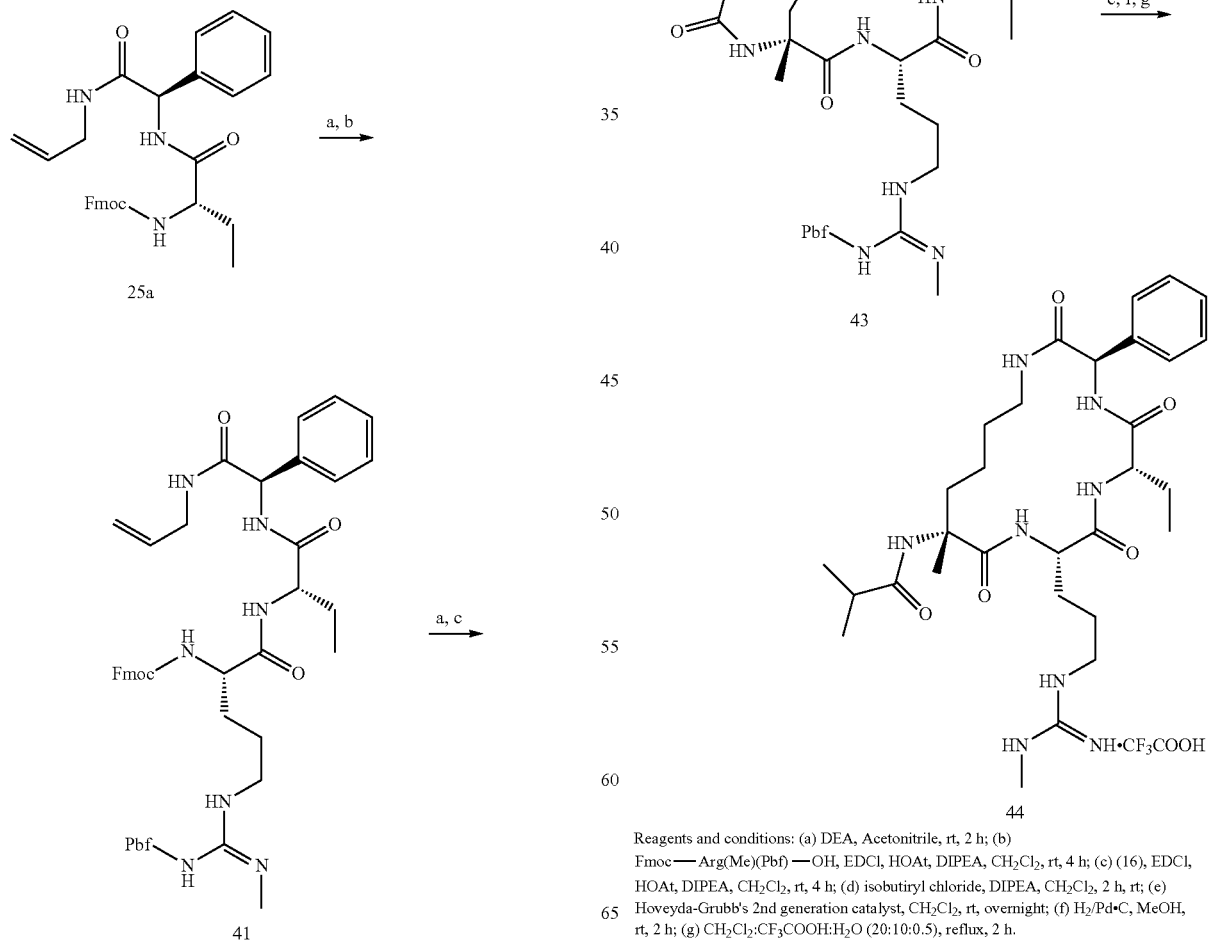

Reagents and conditions: (a) DEA, Acetonitrile, rt, 2 h; (b) Fmoc—Arg(Me)(Pbf)—OH, EDCl, HOAt, DIPEA, CH$_2$Cl$_2$, rt, 4 h; (c) (16), EDCl, HOAt, DIPEA, CH$_2$Cl$_2$, rt, 4 h; (d) isobutiryl chloride, DIPEA, CH$_2$Cl$_2$, 2 h, rt; (e) Hoveyda-Grubb's 2nd generation catalyst, CH$_2$Cl$_2$, rt, overnight; (f) H$_2$/Pd•C, MeOH, rt, 2 h; (g) CH$_2$Cl$_2$:CF$_3$COOH:H$_2$O (20:10:0.5), reflux, 2 h.

Binding Assay

Protein Expression and Purification for the Binding Assay

N-terminal His-tagged WDR5Δ23 (residues 24-334) was expressed from the pET28-MHL vector in Rosetta2(DE3) pLysS cells (Novagen). Cells were grown to $OD_{600}$=0.4-0.6 in 4 L 2×TY at 30° C., induced with 0.1 mM IPTG at 16° C. for 16 hours and harvested in 20 mM HEPES pH 7.5, 500 mM KCl, 10% glycerol, 0.1 mg/ml PMSF, 0.05% NP40. Cells were lysed by addition of 0.2 mg/ml hen egg white lysozyme followed by sonication and clarification by centrifuging for 30 minutes at 15,000 rpm. The resin was washed 3 times for 10 minutes with 40 ml lysis buffer. His-WDR5Δ23 was eluted from the resin by 3×15 minute elutions with 20 mM HEPES pH 7.5, 100 mM KCl, 10% glycerol, 250 mM imidazole pH 7.5. Eluates were clarified by centrifugation at 2000 rpm for 1 minute, syringe-filtered through a 0.45 μM membrane (Millipore), then loaded onto two 5 ml SP-Sepharose Hi-Trap columns using the AKTApurifier (GE Healthcare). Fractions were eluted in 20 mM HEPES pH 7.5, 10% glycerol with a KCl gradient from 0-1000 mM and peak fractions were pooled and concentrated to 64 μM using an Amicon Ultra centrifugal filter, 10,000 MWCO (Amicon). Concentrated protein was aliquoted and samples were frozen on dry ice and stored at −80° C.

FP Based Experiments

All the FP based experiments were performed in MICROFLUOR® 2 Black, "U" Bottom, 96-well Microtiter Plates (ThermoSci.) and FP was measured as mP units in a microplate reader (Tecan Ultra) with excitation at 485 nm and emission at 530 nm. The $IC_{50}$ value of the inhibitors were calculated using GraphPad Prism 4 software.

Competitive Binding Experiments

The binding affinities of the synthetic peptides shown in the study were measured using this competitive binding assay described earlier (31). A pre-incubated complex solution of WDR5Δ23 and the tracer in 120 μl assay buffer were added to dilutions of the test compound in 5 μl DMSO, giving final concentrations of WDR5Δ23 and the tracer of 4 nM and 0.6 nM, respectively. Three control wells were included in each plate: blank (without protein and tracer), 100% inhibition (tracer only), and 0% inhibition (complex solution only). The plates were incubated with shaking at room temperature. The mP values were measured after five hours of incubation and $K_i$ values were calculated using the equation described previously (32).

REFERENCES

1. Kouzarides, T. Chromatin modifications and their function. *Cell* 2007, 128, 693-705.
2. Jenuwein, T.; Allis, C. D. Translating the histone code. *Science* 2001, 293, 1074-1080.
3. Shilatifard, A. Molecular implementation and physiological roles for histone H3 lysine 4 (H3K4) methylation. *Curr Opin Cell Biol* 2008, 20, 341-348.
4. Sims, R. J., 3rd; Reinberg, D. Histone H3 Lys 4 methylation: caught in a bind? *Genes Dev* 2006, 20, 2779-2786.
5. Wysocka, J.; Swigut, T.; Xiao, H.; Milne, T. A.; Kwon, S. Y.; Landry, J.; Kauer, M.; Tackett, A. J.; Chait, B. T.; Badenhorst, P.; Wu, C.; Allis, C. D. A PHD finger of NURF couples histone H3 lysine 4 trimethylation with chromatin remodelling. *Nature* 2006, 442, 86-90.
6. Huntsman, D. G.; Chin, S. F.; Muleris, M.; Batley, S. J.; Collins, V. P.; Wiedemann, L. M.; Aparicio, S.; Caldas, C. MLL2, the second human homolog of the *Drosophila trithorax* gene, maps to 19q13.1 and is amplified in solid tumor cell lines. *Oncogene* 1999, 18, 7975-7984.
7. Ruault, M.; Brun, M. E.; Ventura, M.; Roizes, G.; De Sario, A. MLL3, a new human member of the TRX/MLL gene family, maps to 7q36, a chromosome region frequently deleted in myeloid leukaemia. *Gene* 2002, 284, 73-81.
8. Hess, J. L. MLL: a histone methyltransferase disrupted in leukemia. *Trends Mol Med* 2004, 10, 500-507.
9. Guenther, M. G.; Jenner, R. G.; Chevalier, B.; Nakamura, T.; Croce, C. M.; Canaani, E.; Young, R. A. Global and Hox-specific roles for the MLL1 methyltransferase. *Proc Natl Acad Sci USA* 2005, 102, 8603-8608.
10. Mishra, B. P.; Ansari, K. I.; Mandal, S. S. Dynamic association of MLL1, H3K4 trimethylation with chromatin and Hox gene expression during the cell cycle. *FEBS J* 2009, 276, 1629-1640.
11. Hombria, J. C.; Lovegrove, B. Beyond homeosis—HOX function in morphogenesis and organogenesis. *Differentiation* 2003, 71, 461-476.
12. Monier, B.; Tevy, M. F.; Perrin, L.; Capovilla, M.; Semeriva, M. Downstream of homeotic genes: in the heart of Hox function. *Fly (Austin)* 2007, 1, 59-67.
13. Jude, C. D.; Climer, L.; Xu, D.; Artinger, E.; Fisher, J. K.; Ernst, P. Unique and independent roles for MLL in adult hematopoietic stem cells and progenitors. *Cell Stem Cell* 2007, 1, 324-337.
14. Ferrando, A. A.; Armstrong, S. A.; Neuberg, D. S.; Sallan, S. E.; Silverman, L. B.; Korsmeyer, S. J.; Look, A. T. Gene expression signatures in MLL-rearranged T-lineage and B-precursor acute leukemias: dominance of HOX dysregulation. *Blood* 2003, 102, 262-268.
15. Harper, D. P.; Aplan, P. D. Chromosomal rearrangements leading to MLL gene fusions: clinical and biological aspects. *Cancer Res* 2008, 68, 10024-10027.
16. Argiropoulos, B.; Humphries, R. K. Hox genes in hematopoiesis and leukemogenesis. *Oncogene* 2007, 26, 6766-6776.
17. Maulbecker, C. C.; Gruss, P. The oncogenic potential of deregulated homeobox genes. *Cell Growth Differ* 1993, 4, 431-441.
18. Waltregny, D.; Alami, Y.; Clausse, N.; de Leval, J.; Castronovo, V. Overexpression of the homeobox gene HOXC8 in human prostate cancer correlates with loss of tumor differentiation. *Prostate* 2002, 50, 162-169.
19. De Vita, G.; Barba, P.; Odartchenko, N.; Givel, J. C.; Freschi, G.; Bucciarelli, G.; Magli, M. C.; Boncinelli E.; Cillo, C. Expression of homeobox-containing genes in primary and metastatic colorectal cancer. *Eur J Cancer* 1993, 29A, 887-893.
20. Hsieh, J. J.; Ernst, P.; Erdjument-Bromage, H.; Tempst, P.; Korsmeyer, S. J. Proteolytic cleavage of MLL generates a complex of N- and C-terminal fragments that confers protein stability and subnuclear localization. *Mol Cell Biol* 2003, 23, 186-194.
21. Patel, A.; Vought, V. E.; Dharmarajan, V.; Cosgrove, M. S. A conserved arginine-containing motif crucial for the assembly and enzymatic activity of the mixed lineage leukemia protein-1 core complex. *J Biol Chem* 2008, 283, 32162-32175.
22. Dou, Y.; Milne, T. A.; Ruthenburg, A. J.; Lee, S.; Lee, J. W.; Verdine, G. L.; Allis, C. D.; Roeder, R. G. Regulation of MLL1 H3K4 methyltransferase activity by its core components. *Nat Struct Mol Biol* 2006, 13, 713-719.
23. Wysocka, J.; Swigut, T.; Milne, T. A.; Dou, Y.; Zhang, X.; Burlingame, A. L.; Roeder, R. G.; Brivanlou, A. H.; Allis, C. D. WDR5 associates with histone H3 methylated at K4 and is essential for H3 K4 methylation and vertebrate development. *Cell* 2005, 121, 859-872.

24. Song, J. J.; Kingston, R. E. WDR5 interacts with mixed lineage leukemia (MLL) protein via the histone H3-binding pocket. *J Biol Chem* 2008, 283, 35258-35264.
25. Patel, A.; Dharmarajan, V.; Cosgrove, M. S. Structure of WDR5 bound to mixed lineage leukemia protein-1 peptide. *J Biol Chem* 2008, 283, 32158-32161.
26. Schuetz, A.; Allali-Hassani, A.; Martin, F.; Loppnau, P.; Vedadi, M.; Bochkarev, A.; Plotnikov, A. N.; Arrowsmith, C. H.; Min, J. Structural basis for molecular recognition and presentation of histone H3 by WDR5. *EMBO J* 2006, 25, 4245-4252.
27. Han, Z.; Guo, L.; Wang, H.; Shen, Y.; Deng, X. W.; Chai, J. Structural basis for the specific recognition of methylated histone H3 lysine 4 by the WD-40 protein WDR5. *Mol Cell* 2006, 22, 137-144.
28. Couture, J. F.; Collazo, E.; Trievel, R. C. Molecular recognition of histone H3 by the WD40 protein WDR5. *Nat Struct Mol Biol* 2006, 13, 698-703.
29. Ruthenburg, A. J.; Wang, W.; Graybosch, D. M.; Li, H.; Allis, C. D.; Patel, D. J.; Verdine, G. L. Histone H3 recognition and presentation by the WDR5 module of the MLL1 complex. *Nat Struct Mol Biol* 2006, 13, 704-712.
30. Trievel, R. C.; Shilatifard, A. WDR5, a complexed protein. *Nat Struct Mol Biol* 2009, 16, 678-680.
31. Karatas, H.; Townsend, E. C.; Bernard, D.; Dou, Y.; Wang, S. Analysis of the binding of mixed lineage leukemia 1 (MLL1) and histone 3 peptides to WD repeat domain 5 (WDR5) for the design of inhibitors of the MLL1-WDR5 interaction. *J Med Chem* 2010, 53, 5179-5185.
32. Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. *Anal Biochem* 2004, 332, 261-273.

What is claimed:
1. A cyclic peptidomimetic compound having a structure

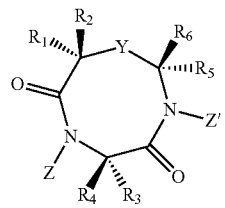

$R_1$ is selected from the group consisting of —H, substituted or unsubstituted $C_{3-7}$ cycloalkyl, and -A-B, wherein A is selected from the group consisting of —NHC(O)—, —N(CH$_3$)C(O)—, —NHS(O$_2$)—, —N(CH$_3$)S(O$_2$)—, —CH═CH—, —C(O)—, —S(O$_2$)—, —CH$_2$NH—, —NHCH$_2$—, —NH—, —CH$_2$N(CH$_3$)— and B is substituted or unsubstituted $C_{1-5}$ alkyl or substituted or unsubstituted $C_{3-7}$ cycloalkyl;

$R_2$ is selected from the group consisting of —H, halo, or $C_{3-7}$ cycloalkyl, either unsubstituted or substituted with one or more of halo, OR, SR, NRR', —(CH$_2$)$_n$—R", n is 0-5, R and R', independently, are selected from the group consisting of —H, $C_{1-3}$ alkyl and $C_{3-7}$ cycloalkyl, and R" is unsubstituted or substituted aryl or heteroaryl, or $R_1$ and $R_2$ can form a ring together with the carbon atom to which they are attached to form a $C_{3-7}$ carbocyclic ring;

Z and Z', independently, are selected from the group consisting of —H, substituted or unsubstituted $C_{1-5}$ alkyl, and substituted or unsubstituted $C_{3-7}$ cycloalkyl;

$R_5$ and $R_6$, independently, are selected from the group consisting of —H, halo, $C_{1-10}$ alkyl or $C_{3-7}$ cycloalkyl, either unsubstituted or substituted with one or more of halo, OR, SR, NRR', —(CH$_2$)$_n$—R", n is 0-5, R and R', independently, are selected from the group consisting of —H, $C_{1-3}$ alkyl and $C_{3-7}$ cycloalkyl, and R" is unsubstituted or substituted aryl or heteroaryl, or $R_5$ and $R_6$ can form a ring together with the carbon atom to which they are attached to form a $C_{3-7}$ carbocyclic ring;

$R_3$ is —(CH$_2$)$_m$—U, wherein m is 1-6 and U is selected from the group consisting of —NH$_2$, —NHCH$_3$, —N(CH$_3$)$_2$, —N$^+$(CH$_3$)$_3$, -DQ-C(═NQ')NP'P", where D is selected from N or CH, and Q, Q', P' and P", independently, are H, substituted or unsubstituted $C_{1-3}$ alkyl, or substituted or unsubstituted $C_{3-7}$ cycloalkyl;

$R_4$ is selected from the group consisting of —H, halo, substituted or unsubstituted $C_{1-3}$ alkyl, and substituted or unsubstituted $C_{3-7}$ cycloalkyl;

Y is substituted or unsubstituted $C_{1-20}$ alkylene or substituted or unsubstituted $C_{3-7}$ cycloalkylene, wherein one or more heteroatom S, O, P, and N, substituted or unsubstituted aryl, or substituted or unsubstituted heteroaryl optionally is inserted, -E-F-G-J-, wherein E and G, independently, are selected from the group consisting of substituted or unsubstituted $C_{1-10}$ alkyl, substituted or unsubstituted $C_{3-7}$ cycloalkyl, —C(O)NH—, —C(O)N(CH$_3$)—, —S(O$_2$)NH—, —S(O$_2$)N(CH$_3$)—, —CH═CH—, —(O)—, and —S(O$_2$)—, F is selected from the group consisting of $C_{1-15}$ alkyl, substituted or unsubstituted $C_{3-7}$ cycloalkyl, and —C(R$_7$)(R'$_7$)—, wherein R$_7$ and R'$_7$, independently, are selected from the group consisting of H, halo, substituted or unsubstituted $C_{1-15}$ alkyl, $C_{3-7}$ cycloalkyl, phenyl, heteroaryl, and a bicyclic group, and J is substituted or unsubstituted $C_{1-15}$ alkyl or substituted or unsubstituted $C_{3-7}$ cycloalkyl, wherein one or more heteroatom, substituted or unsubstituted aryl, or substituted or unsubstituted heteroaryl optionally is inserted;

or a pharmaceutically acceptable salt or hydrate thereof.

2. A compound having a structure

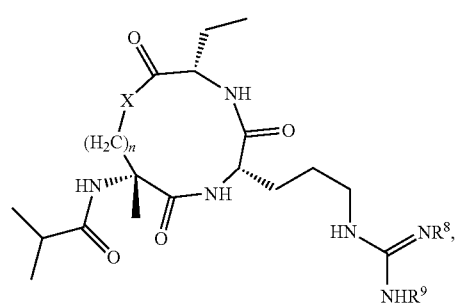

wherein n is an integer 4 through 8, X is NH or

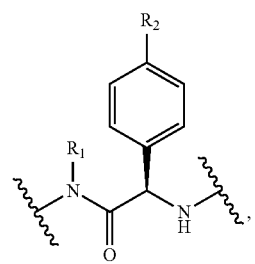

$R_1$ is H or $CH_3$, $R_2$ is H, F or Cl, and $R^8$ and $R^9$, independently, are H, $CH_3$, or $CH_3CH_2$,
or a pharmaceutically acceptable salt or hydrate thereof.
3. The compound of claim 2 having a structure
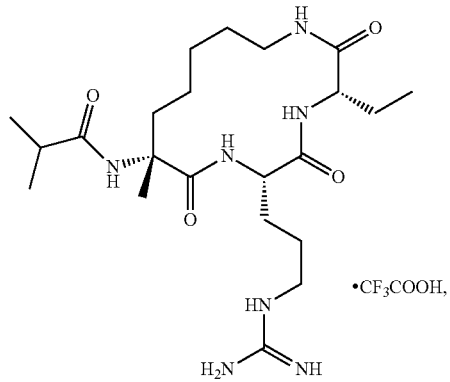
•$CF_3COOH$,
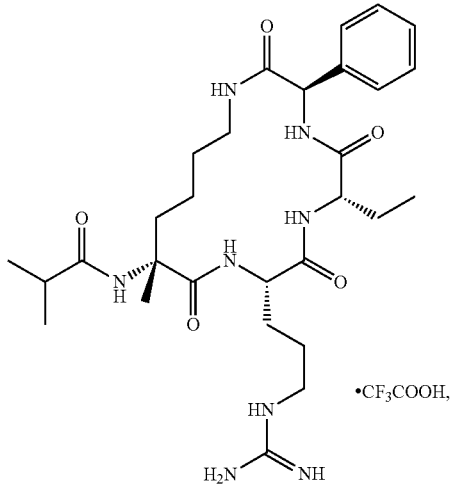
•$CF_3COOH$,
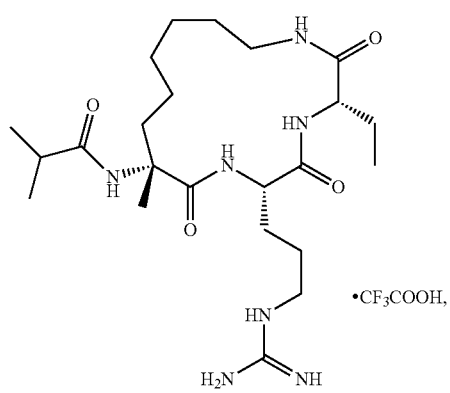
•$CF_3COOH$,
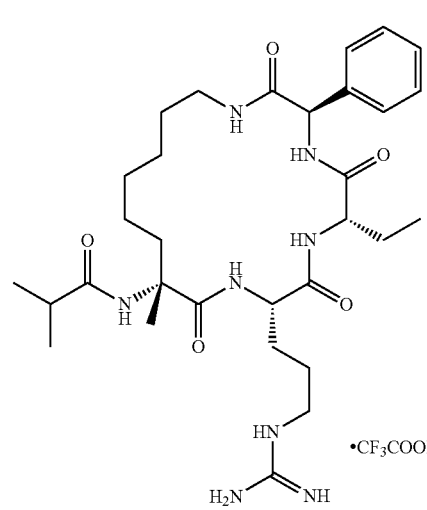
•$CF_3COOH$,
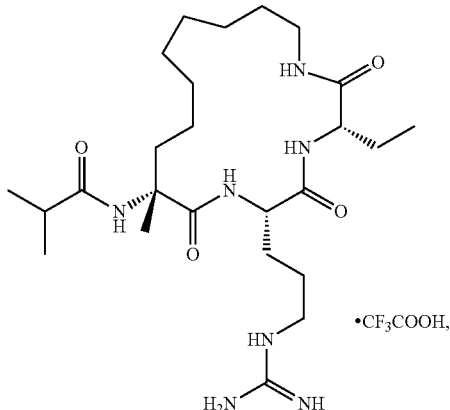
•$CF_3COOH$,
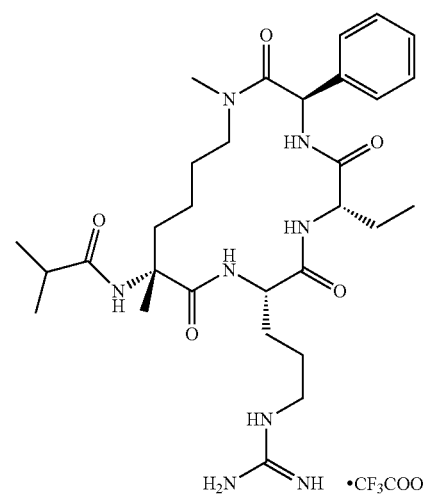
•$CF_3COOH$, 75
-continued
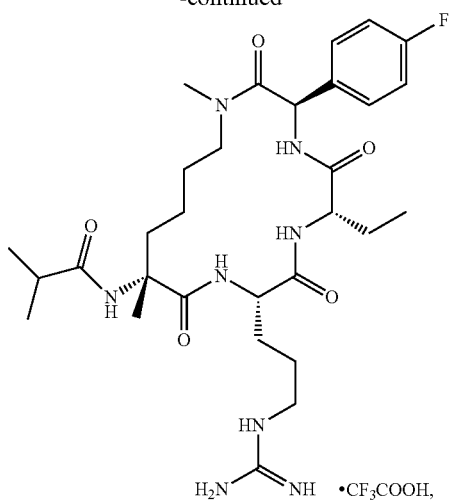
•CF₃COOH,
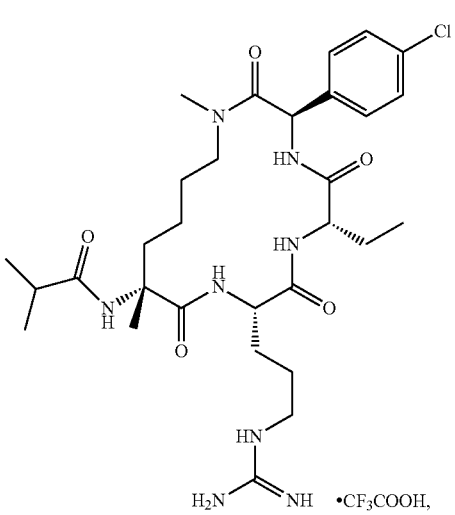
•CF₃COOH,
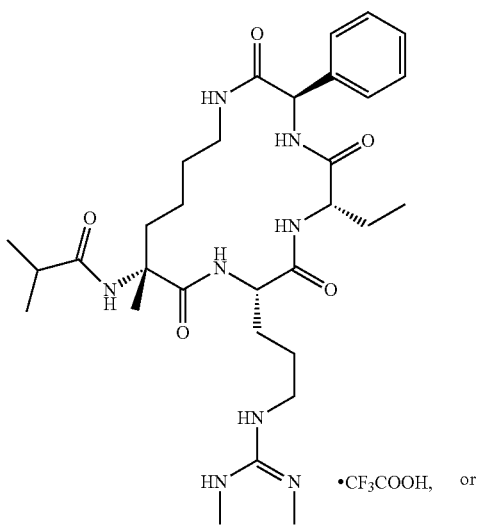
•CF₃COOH, or
76
-continued
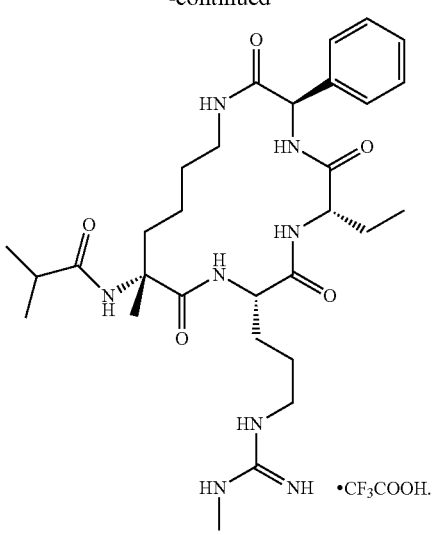
•CF₃COOH.
4. A compound having a structure
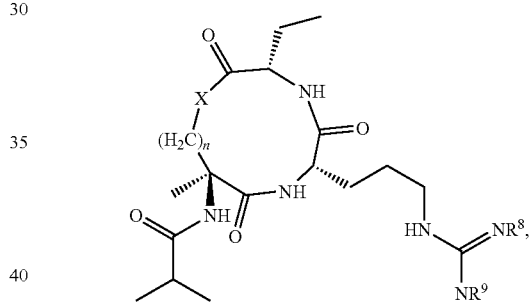
wherein n is an integer 4 through 8, and x is NH or
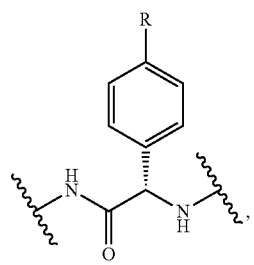
and $R^8$ and $R^9$, independently, are H, $CH_3$, or $CH_3CH_2$
or a pharmaceutically acceptable salt or hydrate thereof.

5. The compound of claim 4 having a structure
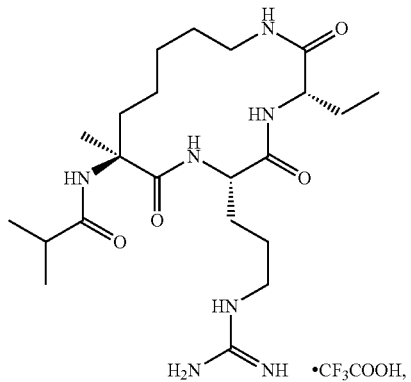
•CF₃COOH,
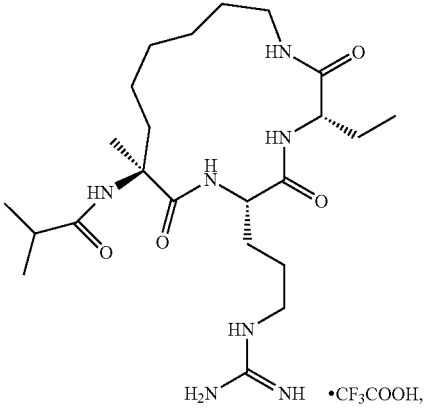
•CF₃COOH,
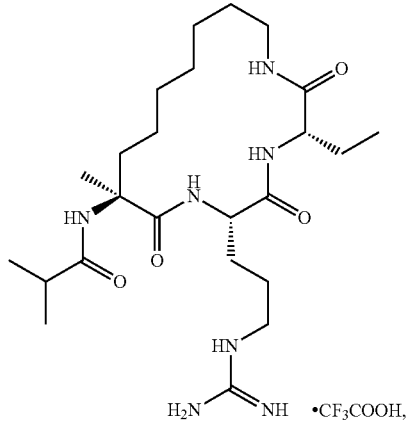
•CF₃COOH,
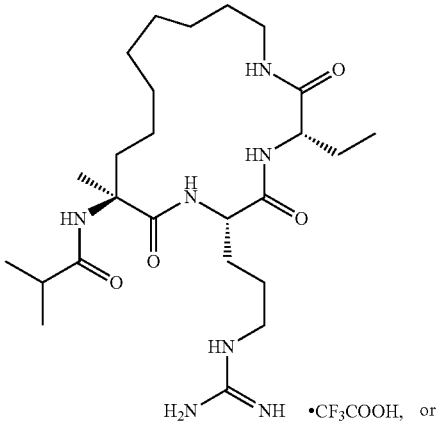
•CF₃COOH, or
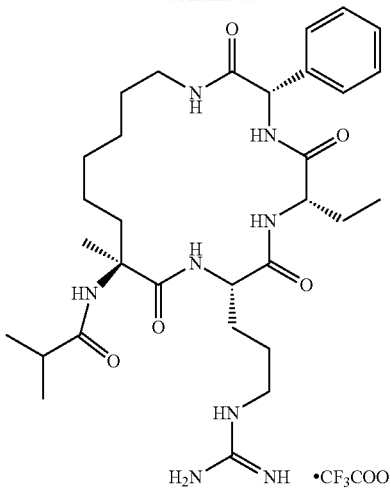
•CF₃COOH.
6. A compound selected from the group consisting of
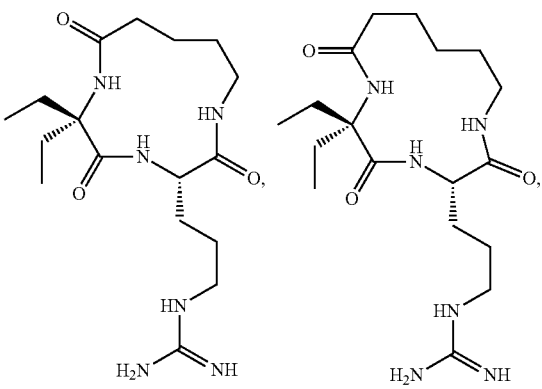
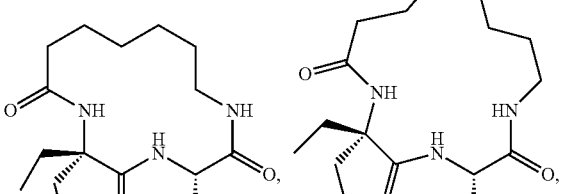
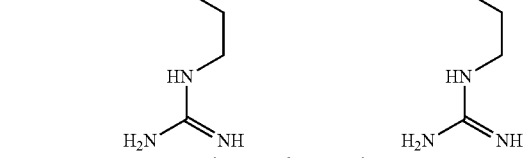
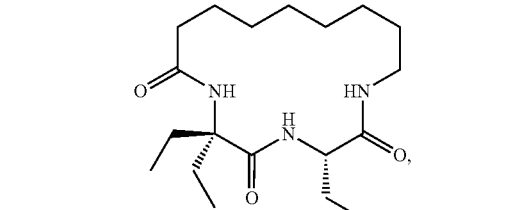
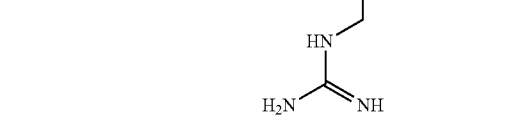

79
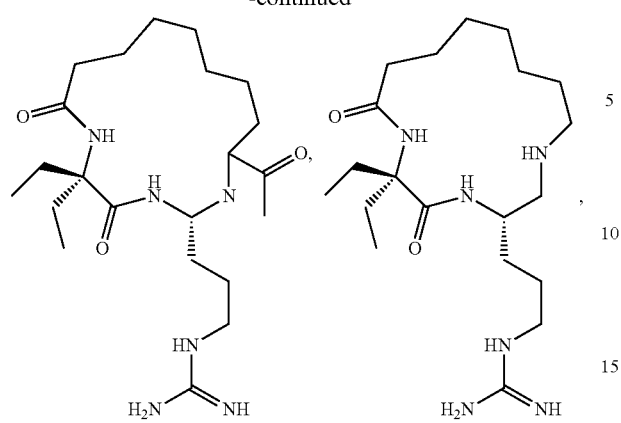
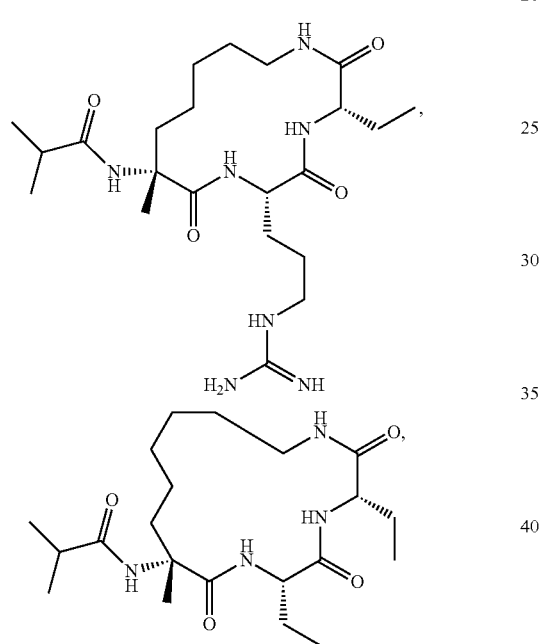
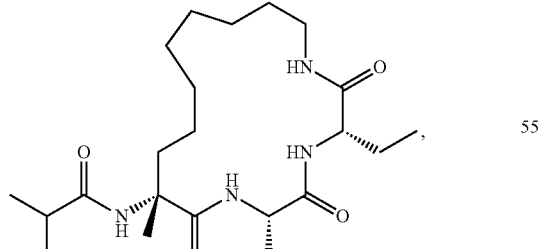
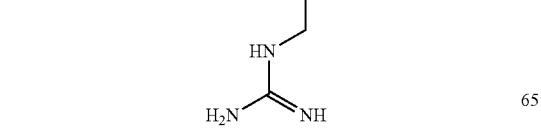
80
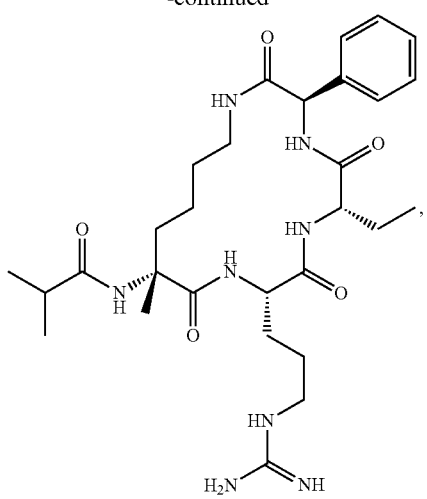
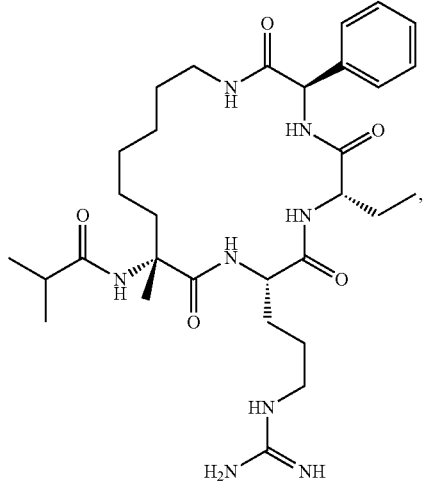
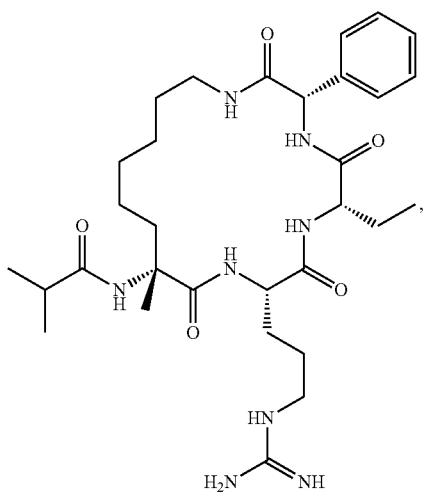

81
-continued
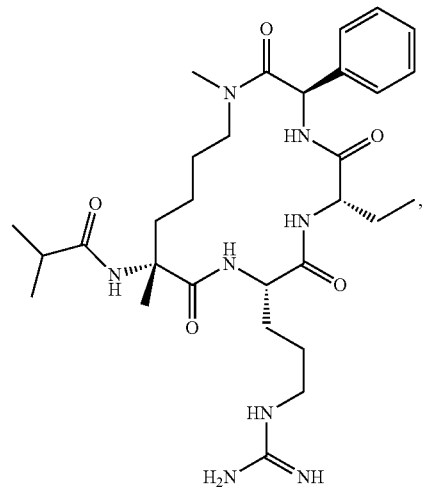
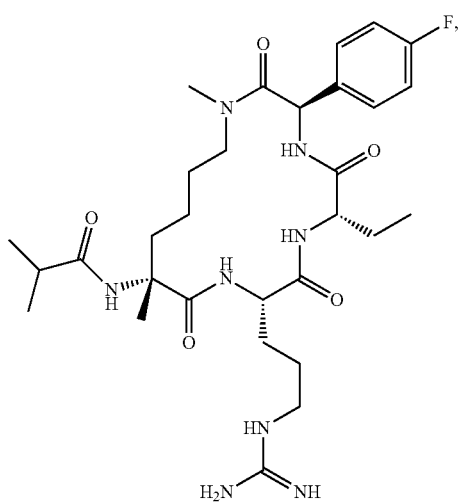
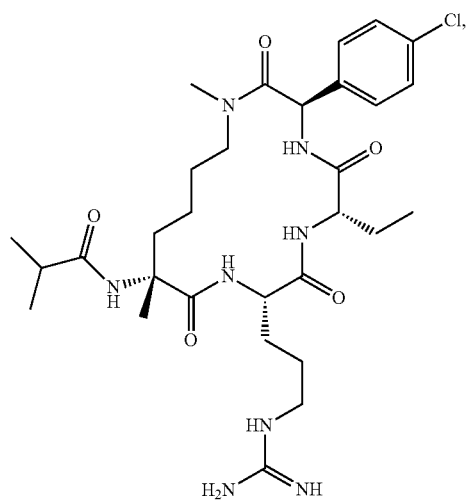
82
-continued
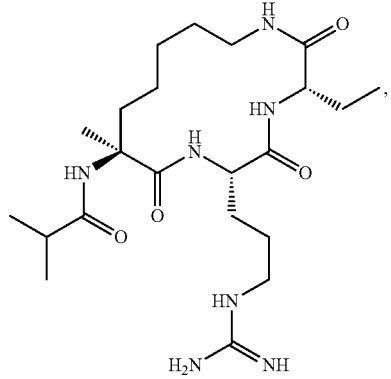
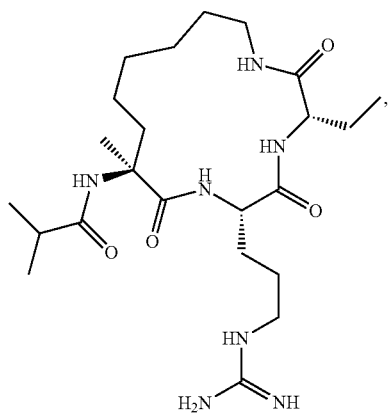
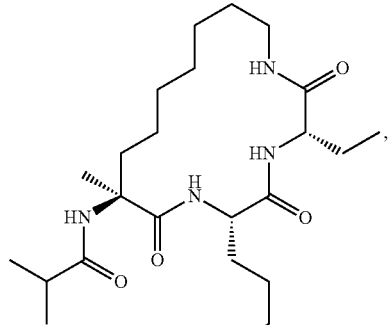
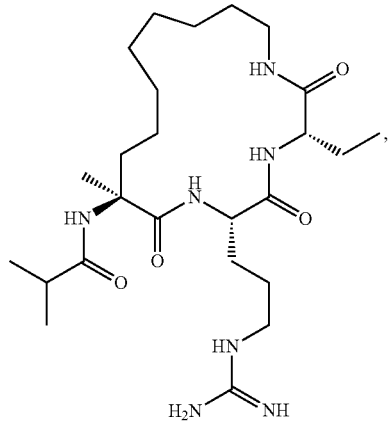

83
-continued
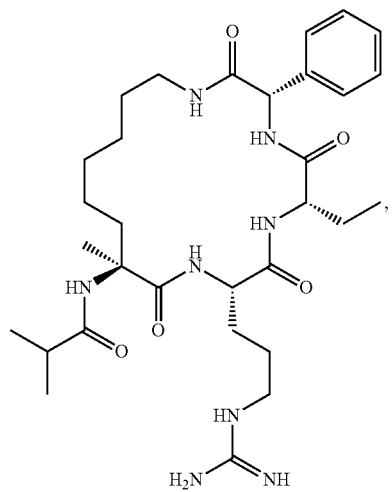
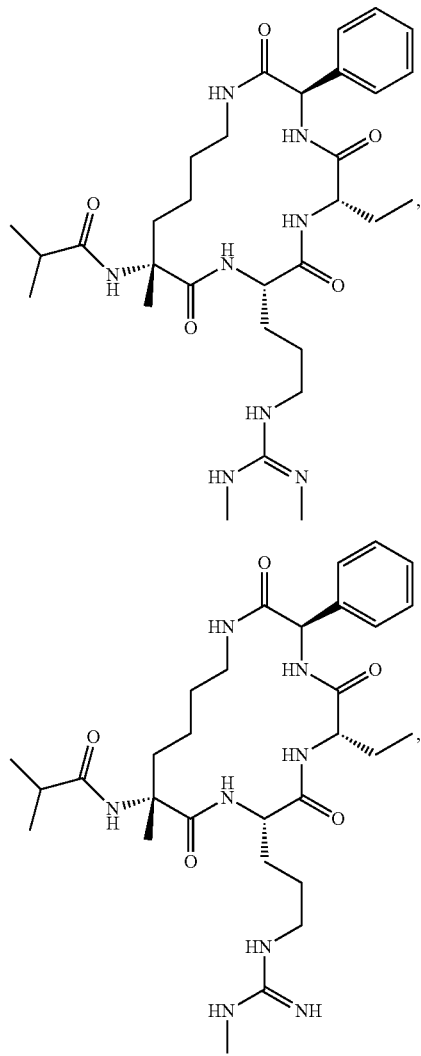
84
-continued
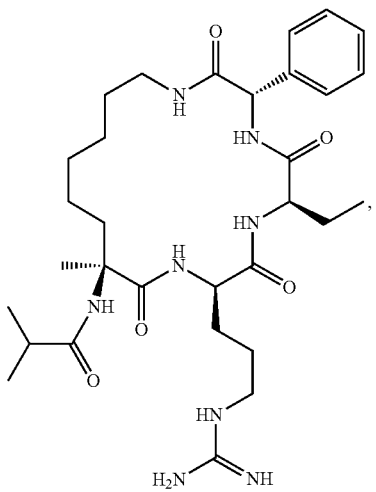
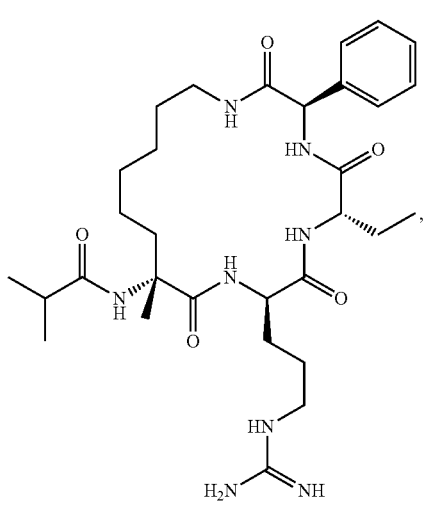
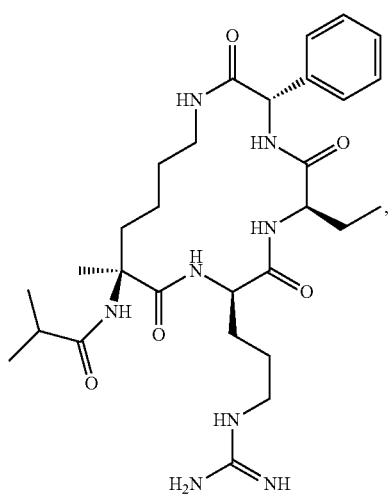

-continued

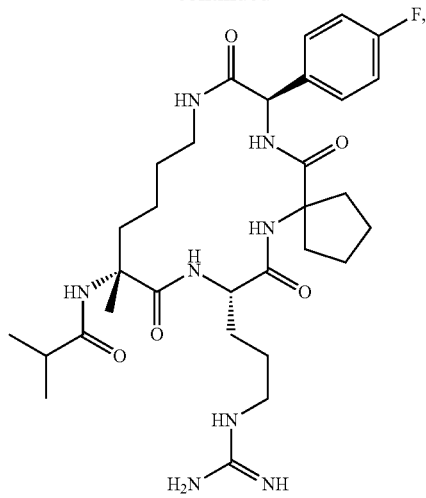

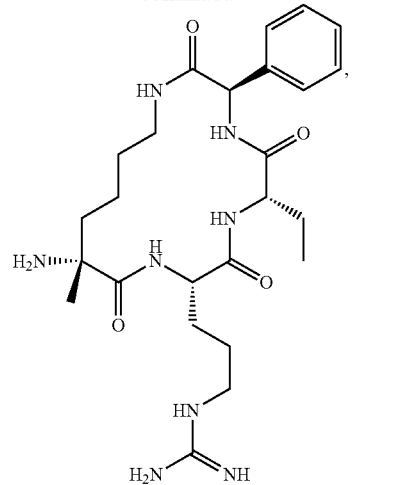

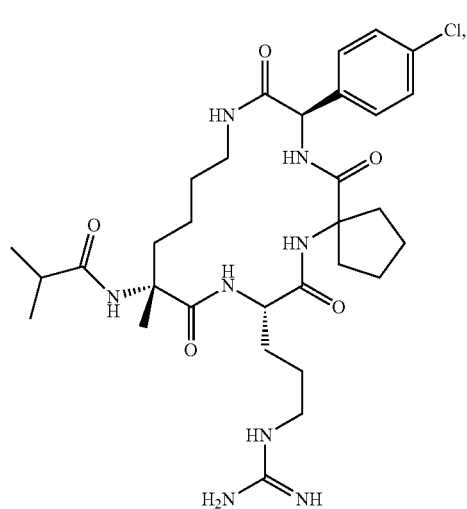

or a pharmaceutically acceptable salt or hydrate thereof.

7. A composition comprising (a) a cyclic peptidomimetic compound of any one of claim 1, 2, 3, 4, 5, or 6; (b) an optional second therapeutic agent useful in the treatment of a disease or condition wherein inhibition of an MLL1-WDR5 interaction provides a benefit; and (c) an excipient and/or pharmaceutically acceptable carrier.

* * * * *